(12) United States Patent
Witkowski et al.

(10) Patent No.: US 8,926,817 B2
(45) Date of Patent: Jan. 6, 2015

(54) PROGRAMMABLE ELECTROPHORETIC NOTCH FILTER SYSTEMS AND METHODS

(75) Inventors: Charles E. Witkowski, Knoxville, TN (US); Jeremy Norris, Knoxville, TN (US); Peter Osucha, Knoxville, TN (US); H. Lee Martin, Knoxville, TN (US)

(73) Assignee: Expedeon, Ltd, Swavesey, Cambridge (GB)

( * ) Notice: Subject to any disclaimer, the term of this patent is extended or adjusted under 35 U.S.C. 154(b) by 855 days.

(21) Appl. No.: 12/967,890

(22) Filed: Dec. 14, 2010

(65) Prior Publication Data

US 2011/0220501 A1 Sep. 15, 2011

Related U.S. Application Data

(63) Continuation of application No. 12/768,586, filed on Apr. 27, 2010, now abandoned.

(60) Provisional application No. 61/173,087, filed on Apr. 27, 2009.

(51) Int. Cl.
*G01N 27/447* (2006.01)

(52) U.S. Cl.
CPC .................. *G01N 27/44713* (2013.01)
USPC ........................... 204/607; 204/608; 204/457

(58) Field of Classification Search
USPC .......................................... 204/457, 607, 608
See application file for complete search history.

(56) References Cited

U.S. PATENT DOCUMENTS

| | | | |
|---|---|---|---|
| 3,271,198 A | | 9/1966 | Winogradoff et al. |
| 4,455,370 A | * | 6/1984 | Bartelsman et al. ......... 435/6.19 |
| 4,715,942 A | | 12/1987 | Tezuka et al. |
| 4,737,259 A | * | 4/1988 | Ogawa et al. ................. 204/606 |
| 5,066,382 A | | 11/1991 | Weinberger et al. |
| 5,217,592 A | | 6/1993 | Jones |
| 5,373,197 A | | 12/1994 | Ptacek et al. |
| 5,449,446 A | | 9/1995 | Verma et al. |
| 5,810,989 A | | 9/1998 | Krihak et al. |
| 6,071,478 A | | 6/2000 | Chow |
| 6,455,007 B1 | | 9/2002 | Mansky et al. |
| 6,494,230 B2 | | 12/2002 | Chow |

(Continued)

FOREIGN PATENT DOCUMENTS

| | | |
|---|---|---|
| JP | S613046 A | 1/1986 |
| JP | H07508096 A | 9/1995 |

(Continued)

OTHER PUBLICATIONS

Tran, et al. "Gel-eluted Liquid Fraction Entrapment Electrophoresis: An Electrophoretic Method for Broad Molecular Weight Range Proteome Separation" Analytical Chemistry, vol. 80, No. 5, Mar. 1, 2008, p. 1568-1573.*

(Continued)

*Primary Examiner* — J. Christopher Ball

(74) *Attorney, Agent, or Firm* — Robert Prince; TechLawLLP

(57) ABSTRACT

An electrophoretic notch filter apparatus including a gel cartridge having at least one sample channel, an electrode and a counter electrode each engagable with the sample channel, a user interface for programming one or more steps for a sample channel into a processor to form a programmed sequence and an electrophoretic controller for implementing the programmed sequence.

50 Claims, 19 Drawing Sheets

(56) References Cited

U.S. PATENT DOCUMENTS

| | | |
|---|---|---|
| 6,494,614 B1 | 12/2002 | Bennett et al. |
| 6,495,104 B1 | 12/2002 | Unno et al. |
| 6,602,661 B1 | 8/2003 | Knezevic et al. |
| 6,783,672 B2 | 8/2004 | Tubbs et al. |
| 6,811,668 B1 | 11/2004 | Berndt et al. |
| 6,919,046 B2 | 7/2005 | O'Connor et al. |
| 6,952,011 B2 | 10/2005 | Brown et al. |
| 6,953,928 B2 | 10/2005 | Vestal et al. |
| 7,030,373 B2 | 4/2006 | Vestal et al. |
| 7,037,419 B2 | 5/2006 | James |
| 7,090,757 B2 | 8/2006 | Thundat et al. |
| 7,211,181 B2 | 5/2007 | Thundat et al. |
| 7,534,338 B2 | 5/2009 | Hafeman et al. |
| 2002/0008058 A1 | 1/2002 | Nugent |
| 2002/0048536 A1 | 4/2002 | Bergh et al. |
| 2002/0094533 A1 | 7/2002 | Hess et al. |
| 2002/0122747 A1 | 9/2002 | Zhao et al. |
| 2003/0070923 A1 | 4/2003 | Schroeder et al. |
| 2003/0135030 A1 | 7/2003 | Guttman et al. |
| 2003/0215855 A1 | 11/2003 | Dubrow et al. |
| 2004/0053049 A1 | 3/2004 | Tsunashima et al. |
| 2004/0265186 A1 | 12/2004 | Clark et al. |
| 2005/0000811 A1 | 1/2005 | Luka |
| 2005/0010375 A1 | 1/2005 | Gallagher |
| 2005/0016852 A1* | 1/2005 | Amirkhanian et al. ....... 204/600 |
| 2005/0116161 A1 | 6/2005 | Hafeman et al. |
| 2006/0165559 A1 | 7/2006 | Greenstein et al. |
| 2006/0219558 A1 | 10/2006 | Hafeman et al. |
| 2007/0258864 A1 | 11/2007 | Braymer et al. |
| 2009/0090630 A1* | 4/2009 | Liu et al. ...................... 204/604 |

FOREIGN PATENT DOCUMENTS

| | | |
|---|---|---|
| JP | 2005535895 A | 11/2005 |
| WO | 9325899 A1 | 12/1993 |
| WO | 0045168 A1 | 8/2000 |
| WO | 0116587 A1 | 3/2001 |
| WO | 03025578 A2 | 3/2003 |
| WO | 03062815 A1 | 7/2003 |
| WO | 03078452 A1 | 9/2003 |
| WO | 2004017061 A1 | 2/2004 |
| WO | 2004113924 A2 | 12/2004 |
| WO | 2009046526 A1 | 4/2009 |

OTHER PUBLICATIONS

Office Action issued by the JPO in Japanese patent application No. 2012-508597 dated Nov. 11, 2013—Engl summary and translation only.

Office Action and Search Report issued by SIPO in Chinese patent application No. 201080018845.3 dated Aug. 21, 2013—incl Engl summary.

International Search Report issued by the EPO in PCT/US10/32598 dated Jun. 30, 2010.

Extended European Search Report issued by the EPO in PCT/US10/32598 dated Sep. 26, 2013.

\* cited by examiner

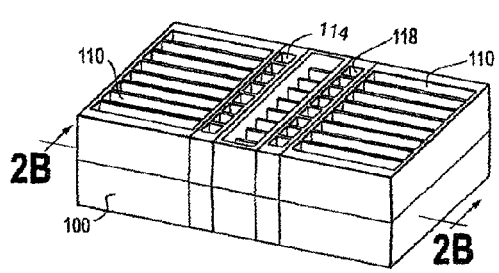
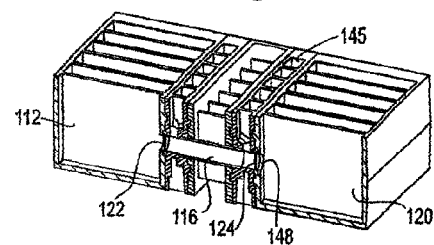
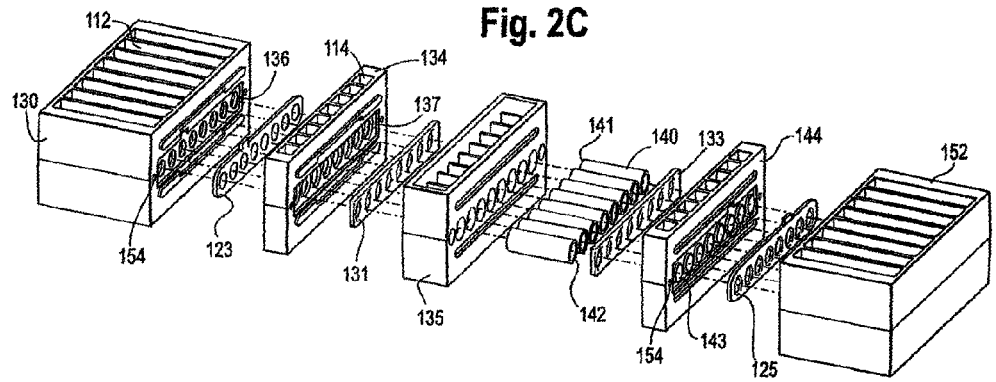

PROGRAMMABLE ELECTROPHORETIC NOTCH FILTER SYSTEMS AND METHODS

This application is a continuation of U.S. application Ser. No. 12/768,586, filed on Apr. 27, 2010 which claims priority to U.S. provisional patent application Ser. No. 61/173,087, filed on Apr. 27, 2009, the specifications of which are incorporated herein by reference.

BACKGROUND OF THE INVENTION (1) Field of the Invention

This invention concerns programmable, electrophoretic notch filter systems and methods that are useful in the isolation, purification and fractionation of analytes in solution. The invention generally relates to the field of analyte isolation and purification, and more specifically relates to the tunable electrophoretic isolation, purification, and fractionation of analytes such as proteins, peptides, polypeptides, protein complexes, antibodies, DNA, RNA, or other biological materials prior to subsequent analysis using, for example, mass spectrometry, ELISA, Surface Plasmon Resonance, or other common detection methods known in the art.

(2) Description of the Art

The purification, isolation and fractionation of complex biological samples is a central process required throughout molecular and cellular biology, pharmaceutical research and development, and medical diagnostics and a host of other fields. For example, in the case of genomics and "next gen" genomic sequencing, DNA fragments must be separated by size and targeted size fragments isolated for the robust creation of DNA sequencing DNA libraries.

In the field of "discovery proteomics," defined as the global identification and quantification of all the proteins found in a biological sample, samples must be reproducibly fractionated according to a known and predictable physiochemical characteristic so as to reduce the dynamic range and complexity of the sample and enable sensitive analysis using methods such as liquid chromatography-tandem mass spectrometry (LC-MS/MS). The abundance range of known plasma proteins, for example, spans over 10 orders of magnitude. Taken together with the heterogeneity introduced by post-translational and post-transcriptional modifications, the detection of low abundance proteins in complex multi-analyte samples remains a tremendous challenge and limits the discovery and validation of analytes that may serve as novel biomarkers and/or drug targets and further limits the deconvolution of cellular and molecular pathways.

In the field of "targeted proteomics," in which the aim is generally to quantify one or more target proteins found in a biological sample, such as human plasma, target protein(s) must be significantly enriched—often by a factor of a million or more—relative to other proteins found in the sample so as to increase signal to noise and permit sensitive quantification, often using LC-MS/MS. Other analytical techniques, such as affinity assays using for example antibodies, require purification either before or after affinity interaction in order to reduce non-specific interactions and permit more robust, sensitive, and reproducible measurements.

In pharmaceutical discovery and development efforts, antibodies and other biotherapeutics must be isolated and purified so that they can be characterized for quality, function, mechanism of action, etc. Further, in molecular biology and biotherapeutic characterization, it is often desirable to purify analytes that interact with a specific protein, compound, or other molecular entity to, for example, deconvolute the therapeutic target and better understand the biological pathway. In these cases, the analyte complex must be purified from the other components in the sample so as to permit sensitive analysis. For these and a multitude of other applications well known to those engaged in these and related fields, methods for the isolation, purification, and fractionation of analytes are required.

A wide variety of methods are known for purifying analytes, such as those that utilize affinity interaction, filtration, electrophoretic separation and chromatographic separation, including but not limited to reverse phase chromatography, gel permeation chromatography, size exclusion chromatography, and cation exchange chromatography.

Generally, when isolating, purifying and fractionating analytes, it is desirable that the system used to do so have a high load capacity, such that a large amount of total analyte can be loaded into the system. Since many target analytes are present at concentrations that are millions of times less than the concentration of the most abundant molecules in the sample, a high load capacity ideally permits preparation of enough sample so as to permit detection of low abundance molecules.

Second, it is usually desirable to provide for the isolation, purification, and fractionation of analytes in a manner that is highly specific and has high resolution. In other words, the preparation system preferably provides for the extraction of the target analyte in as 'neat' of a sample as possible; i.e. ideally only one type of protein is found in a single isolated fraction such that it's signal to noise is optimized.

A further desire is that the method for isolation, purification, and fractionation is highly reproducible, so that the same system and method can be used repeatedly on multiple samples without introducing variability, thereby providing clear and indisputable results. It is also a desire that the methods and system provide for high recovery of, and reproducibility of recovery of, the analytes that have been isolated, purified, and fractionated.

Furthermore, it is desirable that the methods for isolating and purifying analytes be versatile, such that they can be easily adapted to other analytes and are generally useful. For example, methods such as size exclusion chromatography are generally useful for purifying a large range of analytes following some initial method development for each target analyte and may be used to purify multiple analytes or fractions from a single sample in sequential fashion. However, these methods may suffer from relatively poor analyte recovery and poor specificity/resolution. Conversely, affinity purification using a highly specific antibody provides relatively high enrichment, but requires the production of a specific antibody for each analyte targeted for purification.

It is further desirable that any single isolation or purification system/method be compatible with other methods/systems for isolation, purification and fractionation, as multiple dimensions of separation/enrichment are often required. Lastly, it is desirable that such systems and methods be easy to use and easy to optimize for various samples and target analytes.

Perhaps the most widely used method for separating, purifying and isolating charged analytes is one dimensional electrophoresis (1DE), typically using either agarose or polyacrylamide gel electrophoresis (PAGE). 1DE permits the separation of analytes, such as DNA, proteins, peptides, polypeptides, protein complexes, RNA, etc. on the basis of electrophoretic mobility. Under an applied electric field, charged analytes migrate through and are sieved by polymeric gel matrix. As such, analytes with a high mass to charge ratio move more slowly than analytes with a low mass to charge ratio and are thus separated.

Used together with sodium dodecyl sulfate (SDS), a uniform net charge is imparted on all proteins in a sample such that the separation accomplished strictly on the basis of molecular weight, rather than on the basis of mass-to-charge. A multitude of other 1DE methods are well known, including but not limited to clear native PAGE, blue native PAGE, field inversion electrophoresis, counter current electrophoresis, capillary electrophoresis and the like. 1DE may be practiced in a slab gel format, in a tube gel format, or some combination of symmetric or asymmetric formats, as has been well published. As such, 1DE is one of the most widely practiced and generally useful techniques for analyte isolation, purification, and fractionation owing to its ability to provide separation on the basis of electrophoretic mobility or molecular weight, resolving power over a large mass range, ease of use, and versatility.

During the 1DE process, the electric field is typically applied as a constant voltage for a continuous period of time sufficient to allow for complete separation of the sample analytes across the entire length of the gel matrix. The voltage is discontinued only at the end of the experiment, immediately before the most electrophoretically mobile analytes reach the end of the gel. The gels can then be imaged, using fluorescence, dyes or other methods well known in the art, and the location of the separated analyte 'bands' detected. Following detection, one or more bands in the gel may be cut out using a razor blade or other similar tool.

A number of methods are known for then recovering the purified analytes from the extracted gel band. The most widely used methods for gel plug purification rely upon enzymatic or other chemical cleavage of the analytes into smaller components that are diffused from the gel plug pores into a surrounding liquid. This method, while useful, is limited in that large, intact analytes, e.g. proteins, protein complexes, etc., must be cleaved into smaller subcomponents. Thus, direct analysis of the intact analyte is generally difficult, if not impossible. In certain applications involving the analysis of proteins in particular, this limitation prevents the facile analysis of post-translational modifications, truncations, splice variants and other features necessary to fully characterize the gene products in the sample. Additionally, the method is highly labor-intensive and tedious and recovery from the gel plugs is relatively low, estimated to be between 15-60%, severely limiting downstream analysis. These limitations severely limit the method's utility in a range of important applications.

An alternative method of analyte recovery from 1DE involves electro-elution of analytes from the extracted gel plug into a solution or onto a membrane. In this case, the cut gel plug is placed into a chamber and an electric field is directed through the gel plug so as to electrophoretically move the target analyte from the gel and into liquid or a capture support (e.g. capture membrane, reverse phase surface, etc.). While useful for some applications, the electro-elution technique is generally inefficient and unable to recover large molecules with high recovery, as has been well published. The technique is also labor-and-time intensive, since it involves the manual extraction of gel plugs and insertion of those plugs into a second apparatus and running of a second apparatus. The method also often results in excessive analyte dilution.

A third method involves the continuous elution of separated analytes from the end of the gel, most often a tube gel, under an applied electrophoretic field into a flowing stream of liquid. In this mode, analytes are separated on the basis of their electrophoretic mobility through the gel. Rather than discontinuing the voltage before the higher mobility analytes reach the end of the gel and cutting the separated bands from the gel matrix, the voltage is continued so as to elute the separated analytes from the gel matrix. As such, the voltage is applied continuously until the last to elute analytes are eluted from the gel matrix and swept into the collecting liquid flowing at the end of the gel matrix. A robotic fraction collector may be used to move the eluate from one collection vial to another, thereby permitting 'fractionation' of the sample.

This method offers several advantages over other 1DE methods for analyte isolation, purification, and fractionation, chief among them the ability to recovery separated analytes intact, in solution. However, limitations of the continuous elution gel electrophoresis method include usability, reproducibility, and dilution. Since analytes are eluted from the separation medium into a flowing stream of liquid, those analytes that elute from the gel at a slower rate and thus require longer to fully elute from the gel are continuously diluted, which is highly undesirable. Furthermore, since voltage must be applied continuously using these systems and methods, there is no effective method for capturing specific, predetermined analyte fractions in a multiplexed, high throughput format, which is highly desirable. Furthermore, no existing system permits the use of ready-to-use kits that have been manufactured in a consistent, reproducible fashion and which permit consistent results run-to-run. Since analytes are eluted from the gel matrix, rather than 'developed' in a standard 1DE method, a respective analyte's migration time must be exactly the same run-to-run if that analyte is to be isolated and purified in a reproducible manner.

It is thus an object of this invention to overcome the various limitations of the prior art discussed above and to describe a system and methods for the improved isolation, purification, and fractionation of analytes.

SUMMARY OF THE INVENTION

The presently claimed invention is intended to solve one or more of the problems identified above and is easy to use at low cost. In particular, the invention concerns systems that are comprised of a user-programmable, multi-channel electrophoretic power supply, pre-cast polymeric gel matrices useful for separating analytes, and collection chambers with static liquid volumes for retaining separated analytes as they elute from the gels. Together, the systems uniquely permit isolation, purification and fractionation of complex samples and the collection of isolated fractionated analytes in a pre-defined liquid volume using automatic pauses in applied potential based on steps pre-programmed into a sequence through an electronic controller and/or active feedback based on detected analyte migration. Methods are provided for partitioning complex biological samples into pre-determined, user-selectable electrophoretic fractions across a broad mass range and capturing said fractions in a pre-defined liquid volume, or targeting one or more specific analytes for pre-programmed isolation and purification, with recovery of said analytes in a pre-defined liquid volume.

The claimed invention utilizes concepts from continuous tube gel electrophoresis, but is the first invention to incorporate a user-programmable electrophoretic controller that uniquely permits pre-programmed elution and collection of pre-determined analyte fractions. The invention further incorporates unique features for loading samples into a horizontal tube gel separation channel without causing dilution or spreading of the sample, as well as features for trapping eluted fractions in a defined liquid volume without causing dilution or spreading of the analyte fractions. Furthermore, the unique features permit easy recovery from the separation channel with a simple pipette without the potential for trapping bubbles which undesirably impede current flow through the system. The invention further provides for multiplexed sample processing, high reproducibility and high recovery. Together, these features provide a novel, electrophoretically-programmable analyte notch filter and methods for using the same.

More specifically, one aspect of this invention is an electrophoretic notch filter apparatus comprising: a gel cartridge including at least one sample channel, each sample channel including a cathode buffer chamber, a sample introduction chamber, a tube gel including a first end associated with the sample introduction chamber, a sample collection chamber associated with a second end of the tube gel and an anode buffer chamber wherein the cathode buffer chamber, the sample introduction chamber, the gel tube, the sample collection chamber and the anode buffer chamber are capable of ionic electrical contact; a power supply that is engagable with a cathode buffer chamber of each sample channel and anode buffer chamber of each sample channel; a user interface for programming one or more steps for a sample channel into a processor wherein a programmed step includes programming at least one of a current or voltage that is applied across the sample channel during the programmed step and programming the duration of the application of the voltage or current across the sample channel wherein the programmed one or more steps form a programmed sequence; and an electrophoretic controller including the processor for implementing the programmed sequence.

Another aspect of this invention is an electrophoretic notch filter apparatus comprising: a gel cartridge including at least one sample channel, each sample channel including a cathode buffer chamber, a sample introduction chamber, a tube gel including a first end associated with the sample introduction chamber, a sample collection chamber associated with a second end of the tube gel and an anode buffer chamber wherein the cathode buffer chamber, the sample introduction chamber, the gel tube, the sample collection chamber and the anode buffer chamber are capable of ionic electrical contact; a power supply that is engagable with a cathode buffer chamber of each sample channel and anode buffer chamber of each sample channel; a detector for detecting a feature of a sample placed in the gel cartridge sample introduction chamber; an electrophoretic controller for implementing a sequence for at least one sample channel and for receiving feedback from the detector when the detector detects the sample feature, wherein the electrophoretic controller pauses the implementation of the sequence based upon the feedback from the detector.

Still another aspect of this invention is a method for recovering analytes of interest from a biological sample comprising the steps of: forming a gel cartridge including at least one sample channel, each sample channel including a cathode buffer chamber, a sample introduction chamber, a tube gel including a first end associated with the sample introduction chamber, a sample collection chamber associated with a second end of the tube gel and an anode buffer chamber wherein the cathode buffer chamber, the sample introduction chamber, the gel tube, the sample collection chamber and the anode buffer chamber are capable of ionic electrical contact; locating an electrode in buffer solution in the cathode buffer chamber of at least one sample channel; locating a counter electrode in buffer solution in the anode buffer chamber of the same at least one sample channel; programming into a processer one or more steps for the at least one sample channel wherein the programming includes programming at least one of a current or voltage that is applied across the sample channel during the programmed step and programming the duration of the application of the voltage or current across the sample channel wherein the programmed one or more steps form a programmed sequence; and engaging an electrophoretic controller that includes the processor to implement the programmed sequence.

A further aspect of this invention is an electrophoretic notch filter apparatus comprising: a housing for retaining at least one sample channel including a cathode buffer chamber and an anode buffer chamber wherein the cathode buffer chamber and the anode buffer chamber are spaced apart and are capable of ionic electrical contact; a cathode buffer chamber electrode and an anode buffer chamber counter electrode; a user interface for programming one or more steps for electrophoretically separating analytes using the at least one sample channel into a processor wherein a programmed step includes programming at least one of a current or voltage that is applied across the sample channel during the programmed step and programming the duration of the application of the voltage or current across the sample channel wherein the programmed one or more steps form a programmed sequence; and an electrophoretic controller including the processor for implementing the programmed sequence.

DESCRIPTION OF THE FIGURES

FIGS. 2A, 2B and 2C are perspective, front and exploded views respectively of a gel cartridge embodiment of this invention

FIG. 21 is a screen shot of a "Develop/Edit New Method" screen of the electrophoretic controller touch screen interface;

FIG. 22 is a screen shot of a "Develop/Edit New Method" screen of the electrophoretic controller touch screen interface.

DESCRIPTION OF THE CURRENT EMBODIMENT

Figure 1:
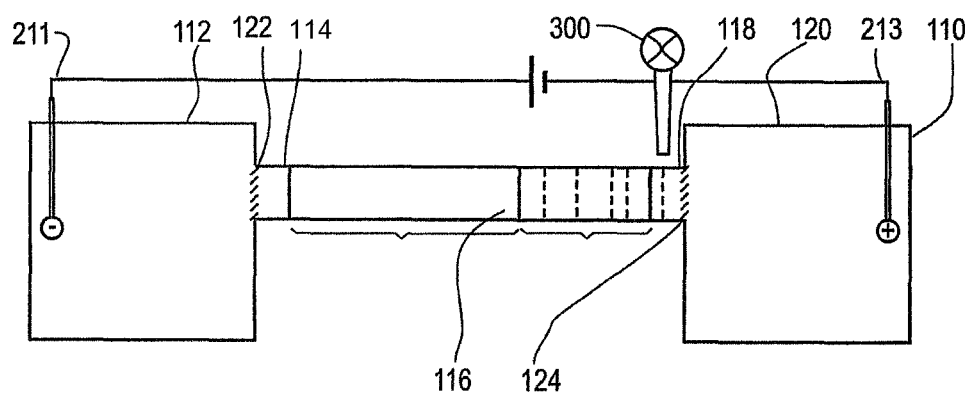
FIG. 1 is schematic view of an electrophoretic notch filter sample chamber embodiment useful in a gel cartridge embodiment of this invention.
Figure 2D:
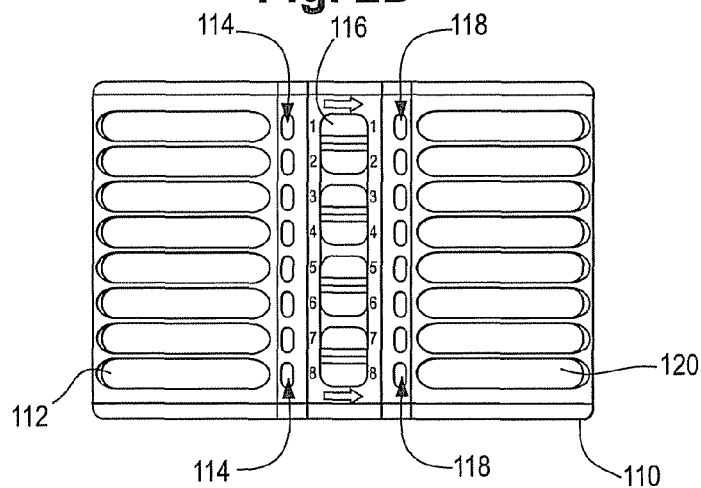
FIG. 2D is an overhead view of a gel cartridge embodiment of this invention.

The present invention relates to programmable, electrophoretic notch filters useful in the isolation, purification and fractionation of analytes in solution. The invention generally relates to the field of analyte isolation and purification, and more specifically relates to the electrophoretically tunable isolation, purification, and fractionation of proteins, peptides, polypeptides, protein complexes, antibodies, DNA, RNA, or other biological analytes prior to subsequent analysis using, for example, mass spectrometry, ELISA, Surface Plasmon Resonance, or other common detection methods known in the art.

The electrophoretic notch filter systems of this invention include three primary components: (1) the programmable electrophoretic controller 200, (2) pre-cast polymeric separation gels, and (3) sample introduction and sample collection chambers that are useful in adding sample or removing fractions without diffusing or diluting analytes. In one embodiment, the separation gels and sample introduction and collection chambers are combined in a single use, multi-channel gel cartridge 100. The electrophoretic controller 200 provides for controlled application of constant voltage or current across each of the gel cartridge channels with pre-programmed fraction collection pauses or dynamic fraction collection control through the use of an integrated detector. The gel cartridge 100 includes a plurality of sample channels 110 where each sample channel is capable of isolating, purifying and/or fractionating one or more analytes of interest from a sample solution including a plurality of analytes.

Together, the system uniquely permits isolation, purification, and fractionation of complex samples and collection of isolated or fractionated analytes in a pre-defined liquid volume using automatic pauses in applied potential based on steps pre-programmed into a sequence through an electronic controller and/or active feedback based on detected analyte migration. Methods are provided for partitioning complex biological samples into pre-determined, user-selectable electrophoretic fractions across a broad mass range and capturing said fractions in a pre-defined liquid volume, or targeting one or more specific analytes for pre-programmed isolation and purification, with recovery of said analytes in a pre-defined liquid volume.

The claimed invention utilizes concepts from continuous tube gel electrophoresis incorporates a user-programmable electrophoretic controller that uniquely permits pre-programmed elution and collection of pre-determined analyte fractions. The invention further incorporates unique features for loading samples into a horizontal tube gel separation channel without causing dilution or spreading of the sample, as well as features for trapping eluted fractions in a defined liquid volume without causing dilution or spreading of the analyte fractions. Furthermore, the design permits easy recovery from the separation channel with a simple pipette without the potential for trapping bubbles which undesirably impede current flow through the system. The invention provides for multiplexed sample processing, high reproducibility and high recovery.

A cross-section of a gel cartridge sample channels 110 is shown in FIG. 1. Each sample channel 110 includes several separate components: a cathode buffer chamber 112, a sample introduction chamber 114, a tube gel 116, a sample collection chamber 118, and an anode buffer chamber 120. The tube gel 116 is generally a hollow tubular structure that includes a pre-cast, porous polymeric gel matrix, such as polyacrylamide, agarose, or other materials or mixtures thereof well known in the art. Preferably, the gel matrix is attached to the side walls of the tube gel tube to prevent gel movement before or during operation, thereby permitting high reproducibility and durability.

The tube holding the gel need not be circular. In fact, the 'tube' may be rectangular, circular, square, or any other geometrical shape in accordance with this invention. Indeed, the term "tube gel" as used herein encompasses gels in tubes having any cross sectional geometry whether circular or not including the geometries discussed in the previous sentence. However, the load capacity of the system is dependent on the cross sectional area of the gel. Furthermore, heat generated during the electrophoretic process may deteriorate the separation and differentially affect viscosity throughout the gel. Therefore, substantially circular tube gels are preferred so as to maximize load capacity and heat dissipation. The cross section may be between 0.1 nm and 50 cm, although the diameter in the preferred embodiment would be between 0.1 mm and 10 mm.

The tube itself may be constructed of most well known materials, including but not limited to plastics, glass, ceramic, or other materials. Glass is generally preferred owing to its heat transfer capabilities, optical transparency, and ease of surface chemistry modification. Importantly, the internal (ID) and outer diameter (OD) of the tube must not vary significantly from tube to tube in order to maximize the reproducibility of separation results, as small fluctuations in ID, for example, may cause significant changes in the current generated through a tube at a given applied voltage, and negatively impact the reproducibility of the separation and elution time.

The polymeric matrix cast in the tube (the gel matrix) may comprise a single porosity throughout the entire tube, multiple discrete porosities, or a gradient of porosities throughout the tube length. The gel matrix may also include embedded antibodies, enzymes, nanoparticles, dyes, or other reacting or non-reacting species useful for a particular application. The gel may be comprised of a range of buffers and conductivities as are well known in the art.

In one preferred embodiment, the gel matrix is comprised of a 'stacking' gel of low porosity, e.g. 3%, and a resolving gel of higher porosity, e.g. 12%. The stacking gel in this embodiment aids in concentrating the sample plug into a sharp band. Once the band reaches the resolving gel, the migration of analytes through the gel is impeded by the smaller pores and analytes will separate according to their respective electrophoretic mobilities. As such, analytes of a higher electrophoretic mobility will reach the end of the separating gel and elute out of the gel before analytes of lower electrophoretic mobility. In this fashion, a subset of the analytes in the sample can be isolated, purified, or fractionated from the other analytes in the sample.

In one embodiment, gel tube 116 includes a polyacrylamide gel matrix cast inside a 6.3 mm I.D. borosilicate glass capillary. The polyacrylamide gel is cast in two layers—a stacking layer and a resolving layer. The stacking layer consists of 3.2% T 5% C cross-linked polyacrylamide and the resolving gel consists of 8% T 5% C cross-linked polyacrylamide, both cast using Tris-Acetate as the gel buffer at pH 7. It can be important that the top of the gel, the interface between the stacking and resolving, and the bottom of the gel all have smooth, flat interfaces that run perpendicular to the electrophoretic current direction so that analyte separation resolution is maximized and bands do not distort, separate sideways, or the like. As such, it is useful to place butanol or a similar agent on top of the gel before it polymerizes to form a planar interface. It can also be important that the gel concentration be uniform throughout the cross section of each layer such that the pore size within a given percentage layer is identical. It is further critical that the length of each aggregate gel be precisely controlled so as to provide reproducibility of elution in accordance with this invention.

The boundary between the cathode buffer chamber 112 and the sample introduction chamber 114, and the boundary between the sample collection chamber 118 and the anode buffer chamber 120 are membranes 122 and 124 that permit an electrophoretic current to pass from the cathode buffer chamber 112 to the anode buffer chamber 120 but that prevent molecules of interest that are introduced into sample introduction chamber 114 from entering either cathode buffer chamber 112 or anode buffer chamber 120. Preferably membranes 122 and 124 are both 500 Da to 3.5 kDa molecular weight cut-off membranes so as to capture substantially all molecules in the sample collection chamber while allowing salt ions in the buffer to pass and thereby carry the electrophoretic current. However any molecular weight cut-off membrane that traps the molecules of interest in the sample from entering the cathode or anode buffer chambers may be used.

Alternatively, larger pore size molecular weight cut-off membranes may be used to allow molecules of a certain pre-selected size to pass through and avoid capture in the sample collection chamber, but retain molecules of a larger size. This option prevents the need to collect a fraction of analytes with an electrophoretic mobility immediately above those of the target fraction, but undesirably necessitates the use of different membranes for the purification of analytes with differing electrophoretic mobilities.

In another embodiment, the membrane is slightly charged to repel molecules from the membrane surface and to prevent non-specific binding. The present invention is not limited to molecular-weight cut-off membranes, but can be effectively utilized with ion exchange, hydrophobic, hydrophilic, affinity capture, and all other membranes that are well known to those skilled in the art.

FIGS. 2A-2D are various views of a gel cartridge embodiment of this invention. Gel cartridge 100 shown includes eight individually isolated sample channels 110 which are essentially identical in design to the single channel 110 shown in FIG. 1 and which together form a unitary gel cartridge incorporating both the tube gels and the means for introducing samples to and collecting fractions from the gel. As show in FIGS. 2A-2D, gel cartridge 100 includes a cathode buffer housing 130 that includes a plurality of discrete cathode buffer chambers 112. Each cathode buffer chamber 112 is sealed except for an aperture 136 at the edge of cathode buffer housing 130 that is associated with sample introduction housing 134. Sample introduction housing 134 includes a plurality of sample introduction chambers 114, each sample introduction chamber including an aperture 137 that passes through sample introduction chamber 114 and that is associated at one end with aperture 136 of cathode buffer chamber 112. A membrane 122 is associated with gasket 123 which in turn is located between cathode buffer housing 130 and sample introduction housing 134 such that membrane 122 in aperture 136 allows for electrophoretic communication between each cathode buffer chamber 112 and anode buffer chamber 120 while preventing migration of analytes of interest into cathode buffer chamber 112. Aperture 137 remains open so that a sample introduced into a sample introduction chamber 114 is in fluid contact with tube gel 116.

Tube gel 116 is generally described above and includes a tubular member 140 that includes a monolithic gel or a gel matrix. Tubular member 140 includes a first opening 141 associated with a sample introduction chamber aperture 137 and a second opening 142 associated with aperture 143 in sample collection housing 144. Sample collection housing 144 includes a sample collection chambers 118 for each channel 110. Each sample collection chamber 118 has an open top 145 that provides a location where analytes of interest are manually or are automatically withdrawn by, for example, using a pipette or other liquid sampling device. Each sample collection chamber 118 has a defined volume in order to ensure the volume reproducibility of the withdrawn samples.

Sample collection housing 144 includes apertures 143 that are associated with aperture 148 in anode buffer chamber 130. A membrane 124 is associated with gasket 125 which lies between apertures 143/148 to physically, but not electrically isolate each sample collection chamber 118 from its adjacent anode buffer chamber 120 in anode housing 152. Additional gasket 131 and 133 assist in forming a liquid seal between central tube gel housing 135 and sample introduction housing 134 and sample collection housing 144 respectively.

The cartridge parts may be machined or molded from a biocompatible polymer having low protein binding properties. For example, the cartridge parts can be made of any machinable or moldable material (ceramic, etc), preferably plastic, more preferably plastics used for low analyte binding and without contaminants such as mold release agents. The cartridge may be formed as a single monolith that accepts a plurality of membranes and tube gels 116. Or the cartridge can be formed from separate housings as described above. In addition, the cartridge and/or cartridge components (buffer chambers) may be single or multi-use. In a multi-use cartridge, the gel tubes may be refillable or replaceable with new gel tubes after a single use.

The tube gels 116 include tubes that are preferably made from borosilicate glass or thin plastic having an inside dimension of 0.1-10 mm in diameter. In a preferred embodiment, the gel(s) located in the tubes will be cast into the gel tubes prior to their assembly of the cartridge, although apparti for accepting tubes that have not been precast according to this invention will be apparent to one skilled in the art. Once assembled, the cartridge components are united to ensure sealing using uniting means such as notchable alignment pins 154 that allow the components to be press fit together to permanently seal the cartridge. Alternatively, a screw pin or other connecting device may be used to non-permanently seal the cartridge.

Once assembled, the cartridge will be filled with storage buffer of a desired pH and conductivity and a plate sealer such as an adhesive Mylar sheet is applied to cover the entire open top of the cartridge in order to keep the gels hydrated until use. The storage buffer is intended to be replaced by the user before the cartridge is placed into use.

To place gel cartridge 100 into use, the plate sealer sheet is removed to expose the various reservoirs and chambers, and the storage buffer is drained from one or more of the channels in the cartridge. Next, the anode and cathode buffer chambers of one or more sample channels are drained and refilled with the appropriate running buffer. Finally, one or more of the sample introduction chambers are loaded with liquid samples including one or more analytes of interest and the cartridge is place in the electrophoretic controller and processed, all as described in more detail below. Sample introduction and fraction collection are facilitated through the use of single- or multi-channel pipette, or via robotic liquid handling stations. The channel spacing is designed to accommodate loading and manipulation of cartridge buffers using standard liquid handling robotics.

A wide variety of gel and buffer systems are suitable for use in the gel cartridge of this invention. Generally the selection of the gel and buffer systems will depend upon the molecular weight ranges of the analytes of interest and the mass resolution required for the desired isolation, purification, or fractionation. For example, a tris-tricine buffer system is useful for resolving proteins having molecular weights between 1 kDa and 300 kDa. Other non-limiting examples of buffer and/or gels that may be used include tris/glycine and tris-acetate/HEPES, bis-tris/MOPS, etc. Native gel systems spanning a variety of pH ranges are available for the separation of proteins and protein complexes under non-denaturing conditions. Agarose gels with TBE or TAE or other common running buffers are useful for DNA and RNA separations.

It is understood that the present invention is not limited to the use of any single gel/buffer system and may be used with any known electrophoresis gel/buffer system. Each of these systems can be further optimized by changing the gel percentage, by the use of gradient gels, by the use of composite gels, or by the use multiple layers of differing gels. The selection of gels and buffers can be made based on one or more of the following criteria: suitability for the selected application, reproducibility, ease of casting, and shelf life. One useful gel buffer system contains a single buffer system, rather than having separate pH buffers in the stacking and resolving gels. This minimizes changes in the performance over time thereby maximizing reproducibility. Additionally, it is also preferred that the gel chemistry chosen allows for an efficient separation using the lowest power possible. If Joule heating is significant, the resolution in the gel suffers and may require active cooling. Without active cooling, keeping the total power consumption per channel to a maximum of 3 Watts, preferably less than 2 Watts, is important to maintain quality separation using the systems of this invention. Certain embodiments of this invention incorporate active cooling of the gel tubes, by for example peltier coolers or recirculating cooled water bath, in which case the wattage per channel can be significantly higher. Buffer conductance, gel length, and gel diameter and porosity are other factors that can impact management of sample channel the power requirements.

Another important component of gel cartridge 100 are membranes 122 and 124 that act as a boundary, retaining the sample in the sample chamber and collection chamber. One class of useful membranes are dialysis membranes. Dialysis membranes are available having a variety of properties. One factor in selecting a membrane includes, but is not limited to, the selection of the proper molecular weight cutoff value to capture the analytes of interest with minimal analyte binding. One preferred membrane material is cellulose acetate, a widely available membrane used for dialysis, which has been shown to have low analyte binding affinity and high stability under the conditions of electrophoresis. An additional membrane characteristic important to the preferred operation of this invention is polarization or charging. It is preferred that the membranes used in the preferred embodiment of this invention are not intrinsically charged and do not become charged under an applied electrophoretic potential. Otherwise, this can induce electro-osmosis across the membrane, causing for example a concentration or dilution of analytes found in the sample introduction or sample collection chambers.

Figure 6A:
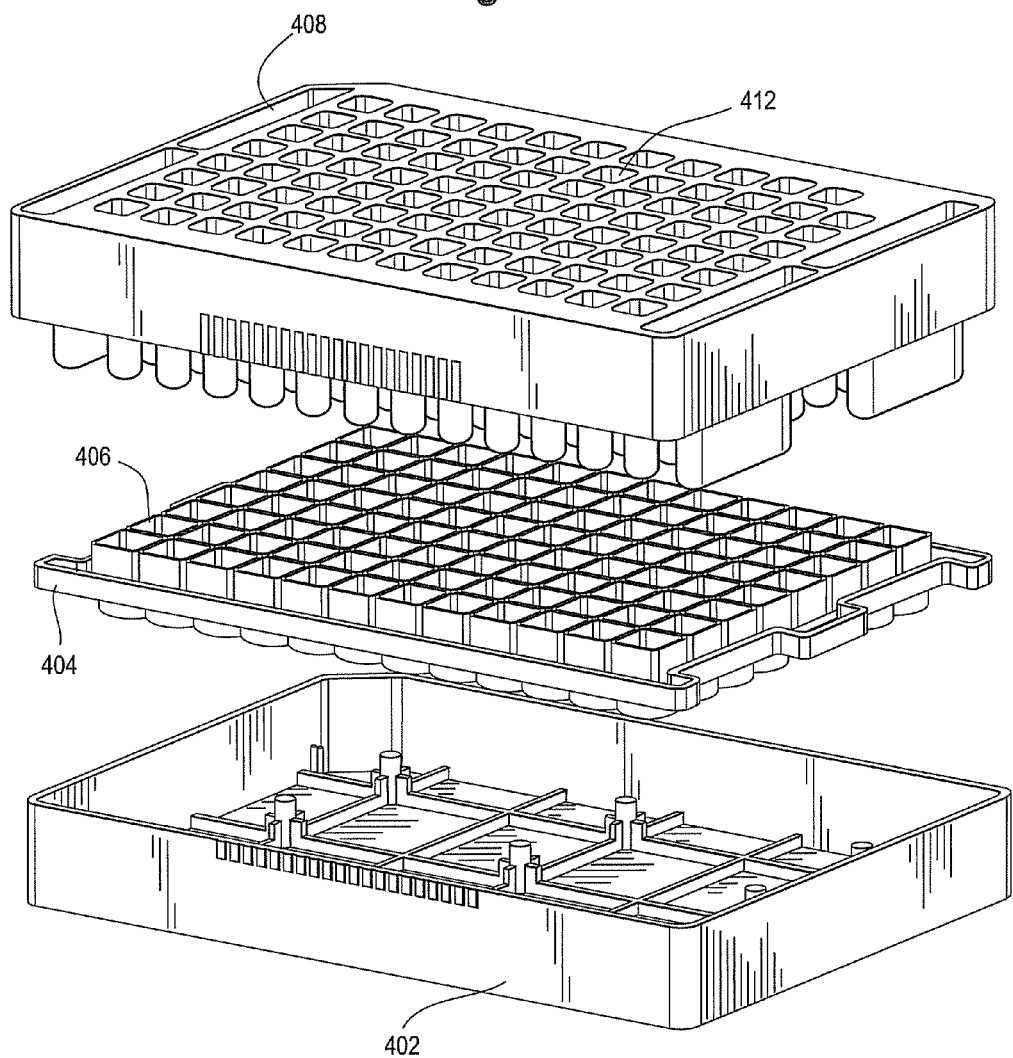
FIGS. 6A and 6B are views of a 96 well plate cartridge embodiment useful in the electrophoretic notch filter apparatus embodiments of this invention.
Figure 6B:
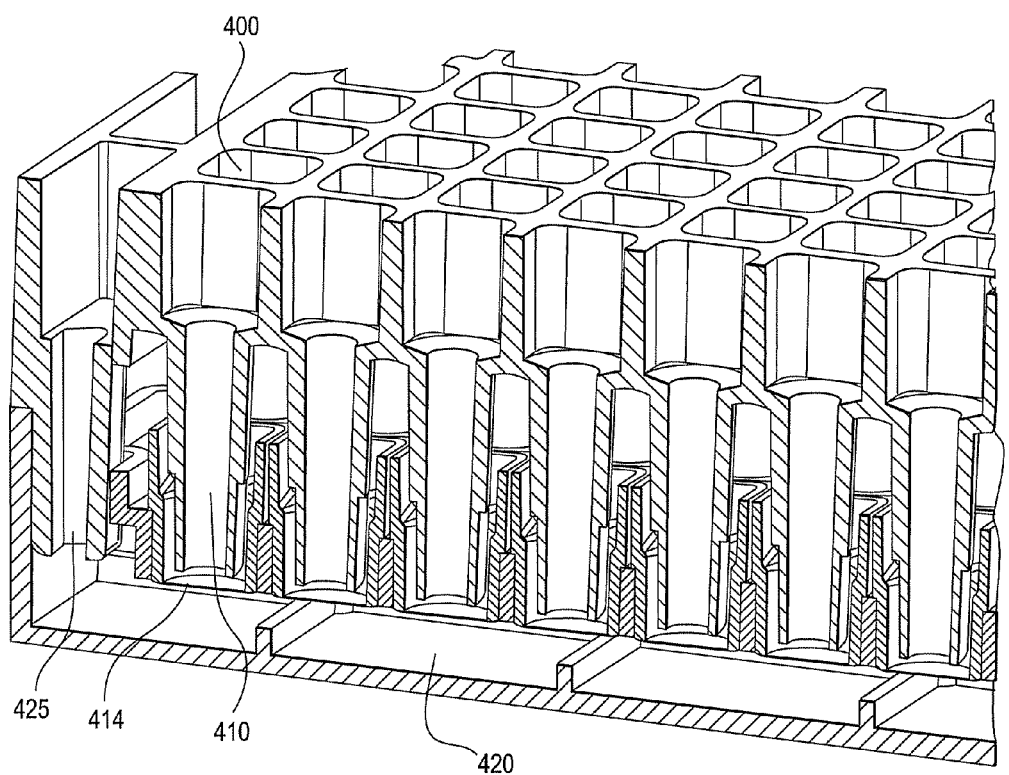

Yet another aspect of this invention is a cartridge system that is useful in high throughput applications such as nLC/MS/MS systems devoted to large scale biomarker discovery programs where increases in fractionation throughput may be necessary. FIGS. 6A and 6B are views of a 96 channel cartridge 400 that achieve the requisite high degree of throughput. The cartridge shown in FIGS. 6A and 6B uses the same general elements present in the eight channel device. In this case, however, the tube gels 410 are turned vertically and formatted in an 8×12 format at 9 mm pitch. This format integrates directly with liquid handling robotics, making it possible to fully automate the preparation of many more samples.

In the cartridge shown in FIGS. 6A and 6B, there is not enough physical space to have independent counter electrodes for every channel. Instead, this design incorporates a common area 420 below the molecular weight cutoff membranes to complete the circuit. This design saves space and allows for the necessary format to interface with existing laboratory equipment.

The cartridge is constructed from molded biocompatible plastic, and has four primary components. A base 402, a sample collection tray 404 including a plurality of sample collection wells 406, and sample well frame 408. Tube gels 410 are cast directly into apertures 412 in sample well frame 408. The volume and length of each tube gel 410 are identical to one another and are preferably identical to that of the 8-channel device. This allows for a sample loading volume of at least 100 μL. Sample is collection tray 404 has a membrane 414 spanning the bottom of the sample well frame 408. The user fills the sample collection tray to the desired volume with buffer prior to loading analyte containing samples. Each sample collection well can accommodate 35-200 μL of buffer. When the sample well frame 408 is seated onto the sample collection tray 404, the tube gels 410 are immersed in the buffer, completing a circuit. Once assembled, the sample is loaded into the well frame directly on top of the tube gel. The area above the sample is filled with buffer to control the pH of the separation. As the voltage is applied, analytes migrate through the tube gel and elute into the sample collection well below. Once the desired molecular fraction has been collected, the voltage is turned off individually to each well or in unison to the entire cartridge, the well frame 408 is removed, and the samples can be transferred from the sample wells 406 to a clean 96 well plate for analysis.

The electrophoretic controller described herein can be modified to accommodate the 96 well cartridge design primarily by modifying the electrode array that provides the current to the electrophoretic cell. In the 96 well design, there will preferably be 96 independent electrodes—each contacting the sample in a sample well—and 4 common electrodes that are inserted into the common return wells 425 on the outside edges of the cartridge.

The degree of isolation, purification or fractionation afforded by the present invention is controlled by the applied electrophoretic current, the length of the sieving matrix, the porosity of the sieving matrix, the pH and conductivity of the gel and running buffers, the operating temperature, and the time that is permitted to elapse before the electric field is paused during a single collection interval. Holding all other variables constant, the collection interval provides user-selectability in the width of the electrophoretic mobility fraction that is collected. The electrophoretic controller of the present invention provides for controlled application of constant or varying voltage or current with pre-programmed collection interval pauses or feedback induced collection interval pauses based on detection of migrating or eluted analytes.

Figure 3:
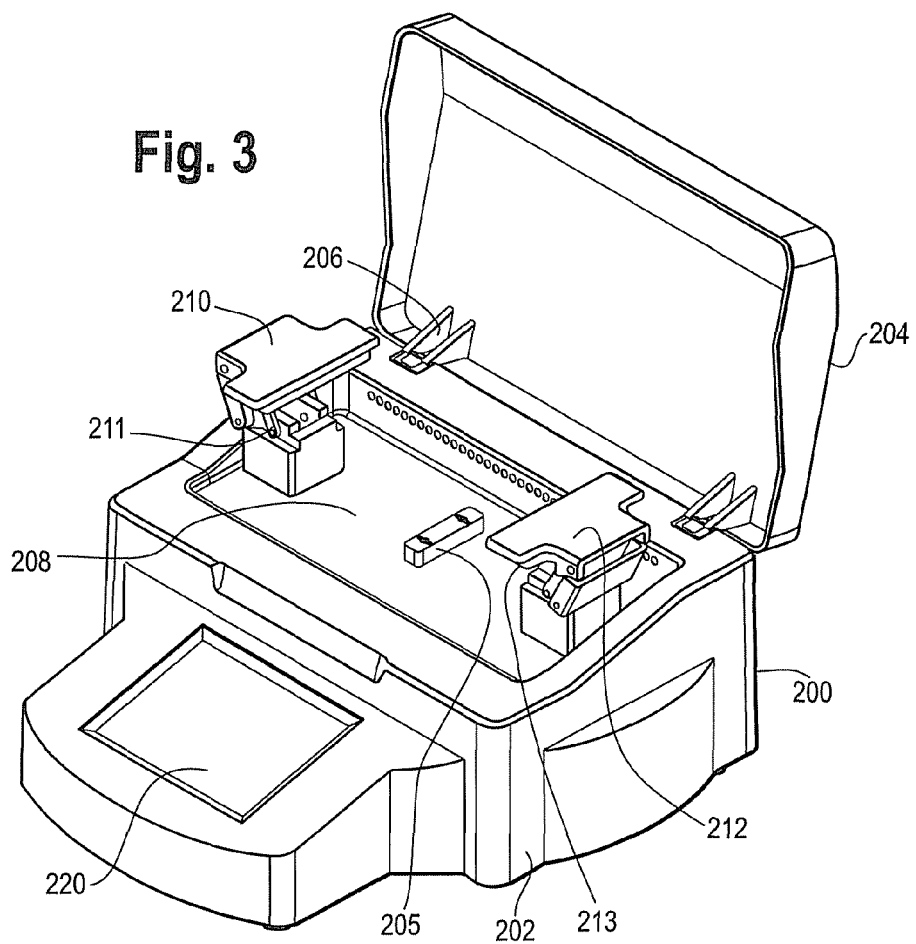
FIG. 3 is a perspective view of an empty electrophoretic controller embodiment of this invention with the lid open.
Figure 4A:
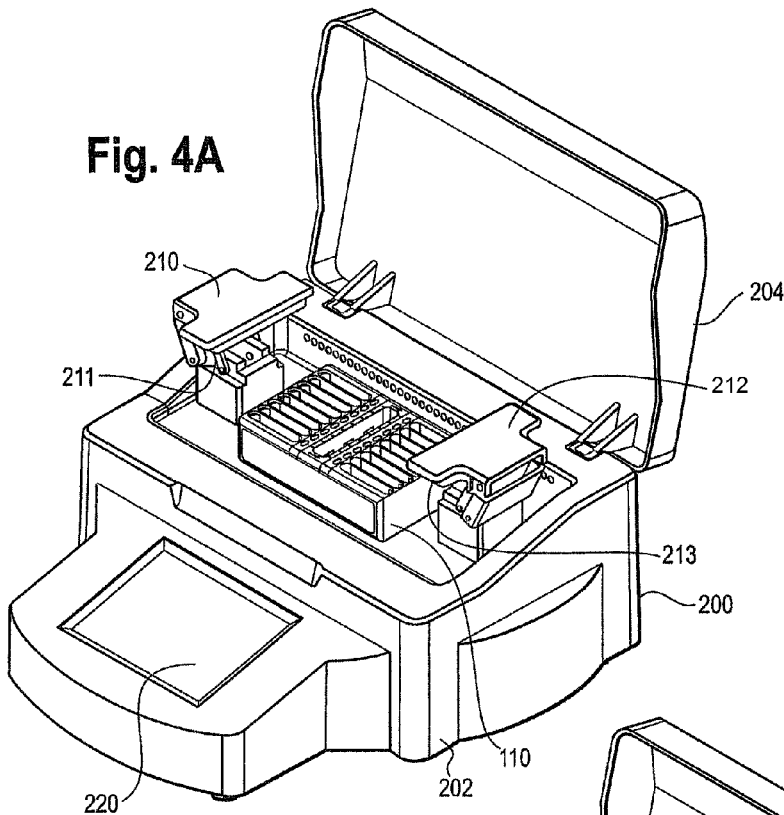
FIG. 4A is a perspective view of an electrophoretic controller embodiment of this invention with the lid open, a gel cartridge in the gel cartridge slot and with the electrode arrays disengaged from the gel cartridge.
Figure 4B:
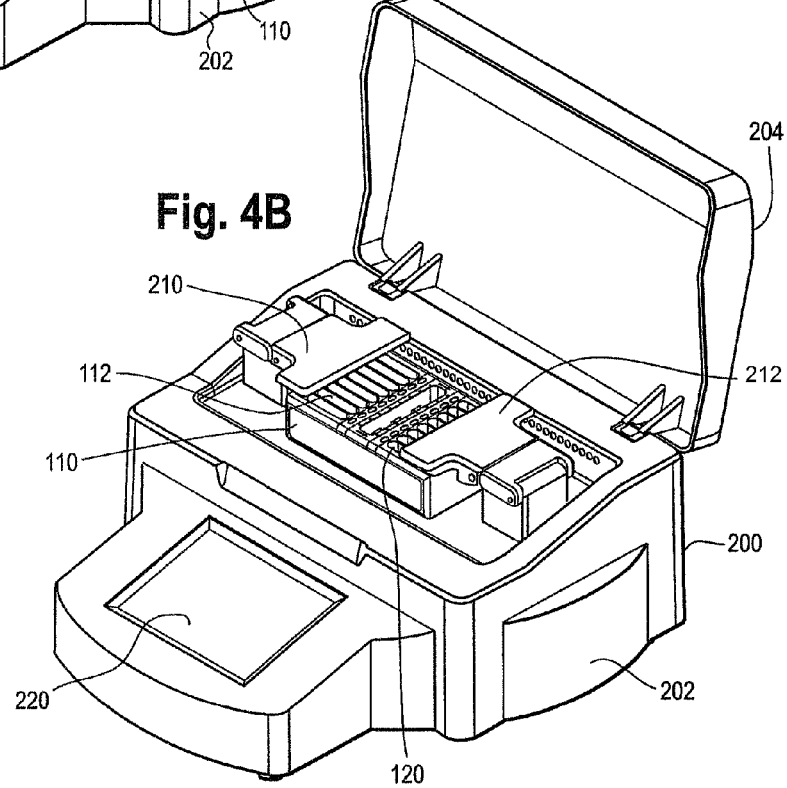
FIG. 4B is a is a perspective view of an electrophoretic controller embodiment of this invention with the lid open, a gel cartridge in the gel cartridge slot and with the electrode arrays engaged with the gel cartridge.

FIGS. 3, 4A and 4B show various aspects of a programmable electrophoretic notch filter controller embodiment of this invention. The electrophoretic controller 200 is an eight sample channel controller, it is bench top in size and it is capable of simultaneously supplying constant current or voltage to each of the eight sample channels 110 in gel cartridge 100 for pre-programmed periods of time.

Electrophoretic controller 200 includes a housing 202 having a movable lid 204. Lid 204 is preferably made of a UV-blocking material, which protects light sensitive analytes. The lid 204 is located top of the instrument and operates on hinges 206. Once lid 204 is open, the gel cartridge 100 will be inserted into a "nest" 208 so as to properly orient the cartridge with the cathode buffer chambers on the left between electrode arrays 210 and 212 as shown in FIG. 4A. It is important that the location of the electrodes within the buffer chambers be the same run-to-run so that the distance between the electrode and counter electrode in each sample chamber is always the same. Following cartridge insertion, an array of electrodes 210 and counter electrodes 212 (eight on each side of the cartridge) are manually or automatically lowered into the cartridge such that an individual electrode 211 is located in each cation buffer chamber 112 and an individual counter electrode 213 is located in each anode buffer chamber 120 as shown in FIG. 4B. Lid 204 is closed and an interlock is engaged that permits application of current/voltage to each individual electrode/counter electrode combination so long as the lid is closed.

A touch screen interface 220 is located on the front of the instrument and allows the user to program the controller as set forth in more detail below. Importantly, the user can program one or more steps for each sample channel to define a sequence of collection intervals. Each step will have a user defined or pre-programmed voltage/current to apply across each individual sample cell 110, as well as a time duration for each programmed voltage/current interval. The programmed collection intervals or steps define the sequence necessary to effect isolation, purification, and fractionation according to the present invention. The applied voltage can be from 1-300V and the time interval can be up to 14400 seconds or more. Collectively, the number of intervals programmed for a given separation will be referred to as a sequence. The system will permit n number of intervals—where n is greater than or equal to 1—allowing for customization of the fractionation process as dictated by the experiment/sample.

To use the system, the user will program the sequence or will choose from a menu of a pre-programmed sequences for each of the eight electrophoretic cells and will start the experiment using touch screen interface 220. The device is programmed to automatically pause the application of the voltage to the sample channel 110 whenever the time interval expires for the step. This allows a user or a robot to extract a sample fraction of interest from sample collection chamber 118 of the appropriate sample channel. The system of this invention is versatile in that the programmed sequences for each sample channel are individually programmed so that all of the sample channels can be performing the same or different sequences simultaneously.

In an alternative embodiment, the controller includes a means for detecting an analyte or a feature related to an analyte of interest as it or they elute through and or out of the separation gel. Detection apparatuses and methods include but are not limited to UV, IR, absorbance, capacitive differentials, etc. In one embodiment, the feature detected can be one or more molecular weight markers that are added to the sample so as to calibrate and measure the migration and/or elution of analytes from a sample channel. Detector 300 may be used to provide feedback to the controller for user-selected isolation of target analytes. For example, the user may select one or more electrophoretic collection intervals corresponding to the elution of one or more analytes for isolation. As said analytes elute and or migrate from the gel tubes, their position is detected via detector 300 and, at the appropriate time, the electrophoretic current is discontinued such that the one or more analytes may be collected from the sample collection chamber 118, either manually using a pipette or via robotics controlled by the controller.

Measurement information, including applied current and voltage and detected elution over the specified electrophoretic mobility window for the eight channels can be displayed to the user in tabular and graphical form on a display such as a screen or a touch screen interface during the course of a sequence. Additionally, sequence information can be exportable in text delimited format using a serial cable or USB port located on the back of the electrophoretic controller.

Figure 5:
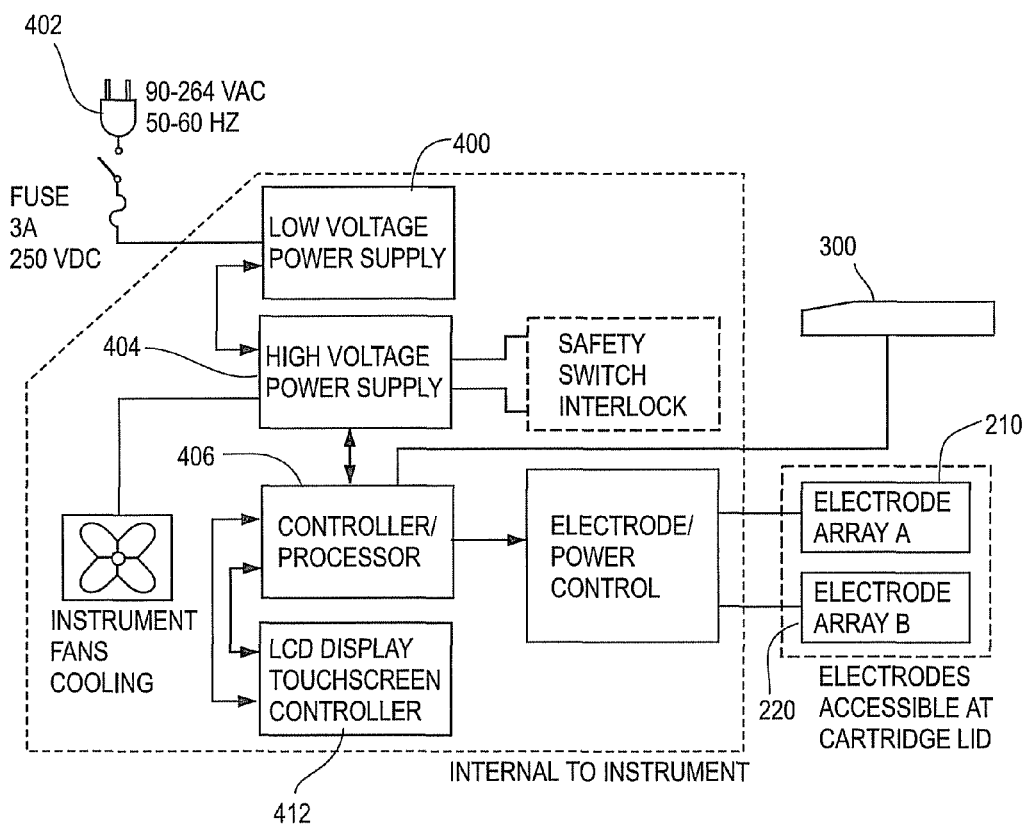
FIG. 5 is a schematic of the electronics of an electrophoretic controller embodiment of this invention.

The electrophoretic controller electronics are shown in FIG. 5. The electronics include a low voltage power supply 400 that is associated with an electrical plug 402. A high voltage power supply 404 is electrically associated with low voltage power supply 402 and it is electrically associated with processor 406. Processor 406 is programmable and is pre-programmed to allow electrophoretic controller 200 to accept use inputs and to operate as discussed herein. Processor 406 interacts with display controller 412 to drive the touch screen graphical user interface 220 and it individually controls—via power control 408—the amount of and/or the duration that voltage and/or current that is directed across the electrodes in each sample channel. Heat generated by the instrument is dissipated using one or more cooling fans 412 located in the rear of the instrument.

Any sample type may be used with the present invention, including but not limited to raw blood, serum, plasma, urine, saliva, tissue homogenates, cell lysates, extractions from food, soil, plants, water, bioprocess components, oil, etc.

For operation, the sample is introduced into the device through the sample introduction chamber. The sample is mixed with a sample buffer, adjusting the volume to fill the sample introduction chamber to a specified volume and buffering the sample pH. The sample buffer may contain reacting agents (DTT, etc.) and/or detergents to aid in the electrophoretic separation. The remaining 3 chambers, the cathode chamber, anode chamber, and sample collection chamber are filled with electrophoresis running buffer. During the separation, the analytes contained in the sample are electrophoretically driven from the sample introduction chamber on the cathode side of the cartridge toward the anode. In one embodiment, the separation is carried out in a polymeric matrix in two phases. To compensate for the large volume of sample introduced into the sample chamber and to maximize resolution, a stacking gel is employed. In this region, the sample is focused into a tight band prior to migration into the resolving region of the gel. The separation of the sample into discrete fractions of molecular weight is accomplished in the resolving gel. As samples are eluted from the end of the resolving gel, they empty into a sample collection chamber of fixed volume bound on one side by the tube gel and on the other side with the ion-permeable membrane specifically chosen to allow buffer ions to pass, but not analytes of interest. The entrapped sample is removed from the collection chamber using a pipette and the sample fraction can be stored for subsequent analysis.

Opening the lid 204 allows access to the cartridge compartment 208 for loading and unloading the cartridge 100 and for collecting fractions during the experiment. The cartridge is loaded, as shown in FIGS. 4A and 4B such that the well numbers imprinted on the cartridge can be read by the operator and arrows imprinted on the cartridge point to the right. The cartridge positioning key 205 prevents the user from loading cartridge 100 in the wrong orientation. The loaded cartridge should rest fully on the bottom of the cartridge compartment 207. With the cartridge in place, the electrode arrays 210 and 212 are lowered in place.

The electrophoretic separation device 200 is controlled by processor 406 using any interface such as a keyboard but preferably using touch screen interface 220. The primary operating modes are (1) method development/editing; (2) method execution; and (3) monitoring. Once the device is powered up, the main central navigation and operating screen will be displayed on touch screen interface 220. The 'Main Screen', shown in FIG. 17 includes the key features necessary for the user to navigate the control software and develop/edit, execute and monitor separation methods.

In one embodiment, the sequence development/editing is accomplished as follows. On the Main Screen, touch the 'Method' button displayed in the upper right hand corner of FIG. 17. This navigates the user to Methods Screen shown in FIG. 18. The user then touches or activates the 'Retrieve' button. This causes the processor to navigate to dialogue screen (FIG. 19) requesting a method number. The user begins by pressing the "C" button on the number pad to clear the existing input. Next, the user enters a method number that has not been used and presses OK. This will cause the processor to display the screen shown in FIG. 20. The user then touches the step number to be modified. This causes the processor to display the input screen shown in FIG. 21. The active cell is highlighted, for example with the color green. The user can then add or modify a value for voltage, current or time can be added or modified by:

a. Cancelling the value in the cell using the C on the number pad.
  b. Entering the desired value.
  c. Touching the inactive cell to activate it. Then repeat step b.
  d. The 'Next' and 'Previous' buttons allow the user to edit the next step or the previous step, respectively. A maximum of 30 steps may be included in any single method.
  e. Touching the OK button when entering/editing is complete.

Figures 19, 20:
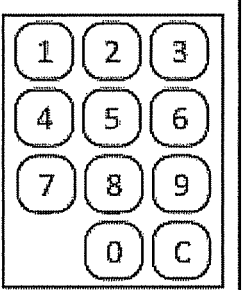
FIG. 19 is a screen shot of the "Retrieve Method" screen of the electrophoretic controller touch screen interface.
FIG. 20 is a screen shot of the "Define New Method" screen of the electrophoretic controller touch screen interface.
Figure 23:
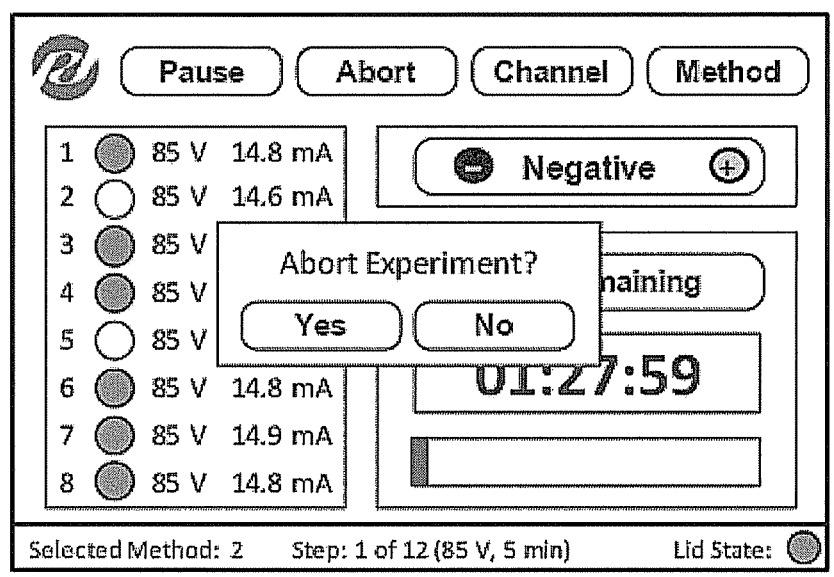
FIG. 23 is a screen shot of a "Main Screen" of the electrophoretic controller touch screen interface including an "Abort Experiment" screen overlay.

Next, the user reviews the voltage or current and time profiles for each step in the newly defined method. If the profile is acceptable, the user presses 'Save' on the Method Screen (FIG. 20). To navigate back to the main screen, the user presses 'Apply' on the same screen.

To edit an existing sequence step, the user follows the steps outlined above, with the following exception. Rather than using a number for a new method, the user enters a number of an existing sequence. The existing method is edited as described above and then saved.

Figures 21, 22:
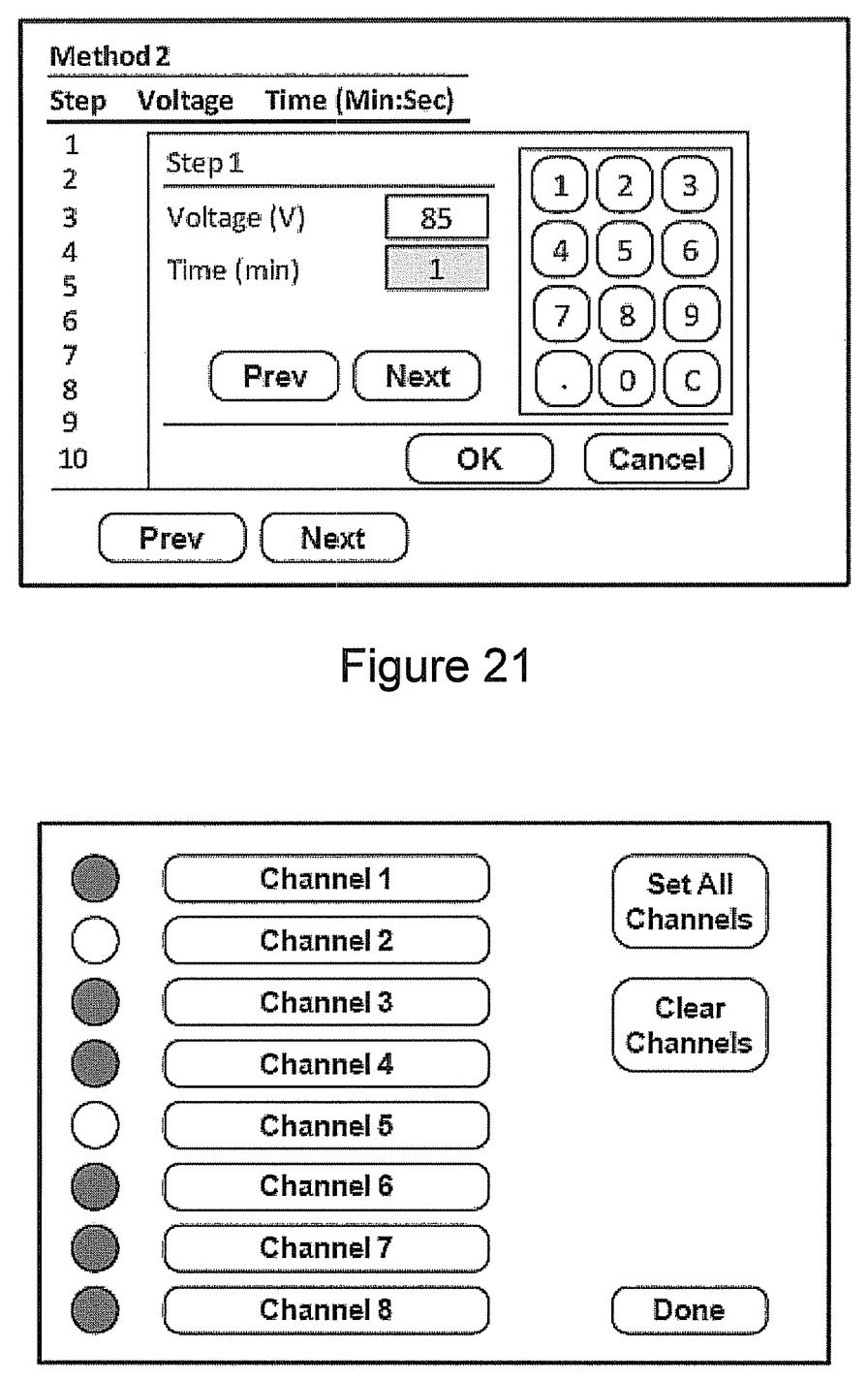

Once one or more steps are inputted and saved for processes performed in one or more sample channels the method(s) consisting of one or more steps can be executed by the user. The methods are executed by the user by pressing the 'Method' button on the Main Screen (FIG. 18) as previously described. Once the method has been selected, the user presses 'Apply' to apply the method and return to the Main Screen—FIG. 17. Next, the user selects the channels to run in the cartridge by pressing the 'Channel' button on the Main Screen. This will bring up the Channel Screen (FIG. 21). From the Channel Screen, the user selects one or more channels—by channel number—to run during the experiment by pressing the corresponding channel button (e.g. 'Channel'), or press 'Select All' to apply the method to all eight channels at once. Once the desired combination of channels has been selected, the user presses the 'Done' button to return to the Main Screen. Finally, the user presses the polarity button on the Main Screen (FIG. 17) to set the polarity of the field. For all experiments using SDS, the polarity will be set at 'Negative.'

Once the sequence(s) have been applied and the channels selected, the user presses the 'Start' button to begin a run. Once running, the 'Start' button becomes the 'Pause' button, which allows the user to pause the run. To completely stop an experiment once it has been started, the user presses the 'Abort' button. A confirmation screen will appear (FIG. 21). To abort the user touches the 'Yes' button. If the user touches the 'No' button, the processor shows the Main Screen and the processing continues.

Figures 17, 18:
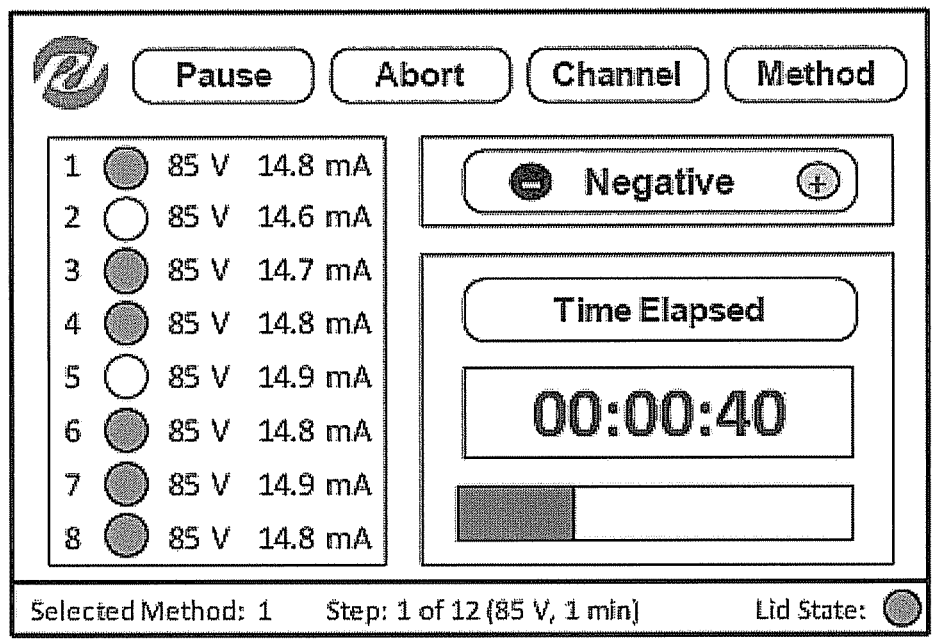
FIG. 17 is a screen shot of the "Main Screen" of the electrophoretic controller touch screen interface.
FIG. 18 is a screen shot of the "Methods Screen" of the electrophoretic controller touch screen interface.

The touch screen interface 220 can also be used to monitor sequences. First the touch screen interface 220 can be used to display channel status. The circles shown in the box on the left side of the screen shown in FIG. 17 depict the status of each channel. A circle around the channel number—preferably colored green—indicates that a channel is active. The applied voltages and currents are displayed to the right of the channel status circles. When the method is paused, the circles will turn a different color such as yellow. If the method fails to start or fails during the run, the circles will turn yet a different color, such as red. When the circles are either yellow or red, the voltage readout is zero.

Time is monitored by touching the "Time Elapsed" button in FIG. 17 above the digital time counter. The user can use the touch screen interface to toggle between 'Time Elapsed', 'Time Remaining' or 'Time To Pause'. A progress bar located below the digital time counter in FIG. 17 provides a visual indication of all time metrics. At the bottom left corner of the Main Screen—FIG. 17, the sequence that is currently selected is displayed. At the bottom center of the Main Screen (FIG. 17), the current step in the sequence that is active is shown (e.g. 'Step i of 12 (85 V, 5 min)). The lid status can also be displayed. A circle—preferably colored green—indicates that the lid is closed (ready/safe to operate) and a different colored circle—such as red—indicates that the lid is open (will not operate).

The cartridge is prepared for insertion into the electrophoretic controller 200 by the general steps of: preparing the sample; preparing the cartridge for the sample; and loading samples into one or more sample introduction chambers 114. The samples are generally prepared by removing salts and known contaminants such as detergents and urea from the sample. The sample can then be placed into sample introduction chamber 114 or it can be further processed by steps such as adding buffers, dilution, adding DTT and so forth. In one method, the sample is further processed by combining it with a sample buffer, water and DTT. The sample can then be added to sample introduction chamber 114 or it can be further processed by steps including heating followed by cooling to give a prepared sample including one or more analytes of interest.

Next, gel cartridge 100 is prepared for sample addition. Gel cartridge preparation begins by removing the plate sealer from the cartridge top. If all eight channels in the cartridge will be utilized in one experiment, then the user removes storage buffer located in every cartridge chamber. If less than all 8 channels will be used, then a transfer pipette or some other device can be used to remove the storage buffer from the compartments associated with only sample channels 110 that will be active during the processing. Next, a running buffer is added to the anode buffer chamber 112 for all active samples channels. Running buffer is also added to the sample collection chamber 118 of each active sample channel 110. The cathode buffer chamber 112 is then filled with running buffer for all active channels. Using a fine-tipped transfer pipette the user then removes and discards any buffer that has flowed from the cathode buffer chamber 112 into the sample loading chamber 114. Finally, 150 µL of the prepared sample is immediately loaded into sample loading chamber 114 or the same channel. The steps above are repeated for the other active channels.

Y(Sigma #C4482-50 mL), 25 µL 1M DTT (Sigma #43816), and 25 µL protease inhibitor cocktail (Sigma #P-8215) were added per 1 gram of yeast cell pellet. The mixture was shaken gently for 30 minutes at room temperature. Insoluble debris were removed by centrifugation at 14,000×g for 10 minutes, followed by filtration through a 5 µm syringe filter (Pall #4650). Protein concentration was measured [DC Protein Assay (Biorad #500-0112)] and the mixtures was aliquotted and store at −80° C. until use. Prior to use, 200 µg aliquot of the sample was diluted with deionized H2O to achieve a volume of 112 µL. To this sample, 8 µL of 1M DTT and 30 µL of sample buffer containing 1% SDS and 25 mM Tris pH 8.5 was added such that the final volume was 150 µL.

The electrophoretic notch filter was prepared in accordance with the invention by casting 8% T 5% C polyacrylamide gel, Tris Acetate into a 6.3 mm I.D., 8 mm O.D. tube gel and polymerized fully. The tube gels were placed into the cartridge with two 3.5 kDa molecular weight cut membranes and the cartridge affixed such that the channels were sealed in electrical and fluidic isolation. Storage buffer comprised of the polyacrylamide gel buffer was used to fill all chambers of the cartridge and a plate sealer was applied.

Immediately prior to use, the plate sealer was removed and the storage buffer removed from the electrophoretic notch filter channel. 8.0 mL of Tris-HEPES SDS running buffer, 0.05M Tris, 0.1% SDS, pH 7.9, was added to the anode and cathode buffer reservoirs of desired channels. A 150 µL aliquot of running buffer was added to the sample collection chamber. Next, 150 µL of the prepared sample was pipetted into the sample loading chamber of the corresponding channel.

To perform the run, the cartridge was placed into the instrument and the electrodes lowered. An electrophoretic notch filter sequence was then created with the steps outlined in Table 1 below.

| Step | 1 | 2 | 3 | 4 | 5 | 6 | 7 | 8 | 9 | 10 | 11 | 12 | 13 |
|---|---|---|---|---|---|---|---|---|---|---|---|---|---|
| Voltage (V) | 50 | 50 | 50 | 50 | 50 | 100 | 100 | 100 | 100 | 100 | 100 | 100 | 100 |
| Fraction Interval (min) | 16 | 41.5 | 2 | 2 | 3 | 2 | 2 | 3 | 5 | 7 | 10 | 15 | 20 |
| Total Elapsed Time (min) | 16 | 57.5 | 59.5 | 61.5 | 64.5 | 66.5 | 68.5 | 71.5 | 76.5 | 83.5 | 93.5 | 108.5 | 128.5 |
| Action/Fraction # | Add RB* | 1 | Change RB/2 | 3 | 4 | 5 | 6 | 7 | 8 | 9 | Change RB/10 | 11 | 12 |

Gel cartridge 100 is then loaded into electrophoretic controller 200 as described above. Next, the electrode arrays are placed into contact with buffer located in the anode and cathode buffer chambers. The lid is closed. And the programmed electrophoretic separation is initiated as described above by the user by touching 'Start' in the Main Screen.

EXAMPLES

Example 1

Broad Mass Fractionation of Yeast Lysate

To demonstrate the unique capabilities of the programmable electrophoretic notch filter of the present invention for broad mass range protein fractionation, a yeast lysate was fractionated into 12 distinct molecular weight fractions and visualized using 1D gel electrophoresis and silver staining, as well as liquid chromatography-mass spectrometry (LC-MS).

To prepare the yeast lysate, the yeast cells were pelleted by centrifugation at 3,000×g for 10 minutes. 2.5 mL Cellytic After Step 2, the system automatically paused for collection of the first pre-defined fraction collection interval, typically corresponding to proteins 30 kDa. Using a pipette, 150 µl was transferred from the sample collection chamber to a collection tube. Any remaining solution was removed from the fraction collection chamber and added to the first 150 µl. The tip was then discarded and the chamber washed with 150 µl running buffer and replenished with 150 µl fresh running buffer. The sequence was then resumed by pressing 'resume' on the instrument's programmable interface. The process was repeated for all remaining fractions using the automatic electrophoretic controller. After steps 3 and 11, the running buffer was changed in the anode and cathode buffer reservoirs to ensure proper pH throughout the system.

Figure 7:
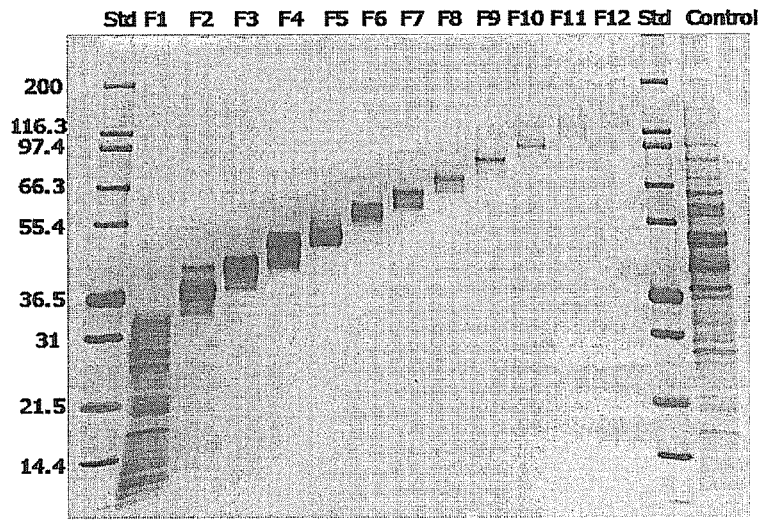
FIG. 7 is a 1D gel visualization of results of fractionation of yeast lysate using a 'mid' mass protein separation embodiment of the current invention across mass range 3.5-150 kDa, with resolution between 30-150 kDa.

To visualize the broad mass range fractionation results on a 1D gel, a 10-20% Tris-Glycine gel (Invitrogen) was prepared according to the manufacturer's instructions. An 8 µL aliquot of each fraction from the electrophoretic notch filter system was combined with 10 µL Tris-Glycine SDS Sample Buffer (2×) and 2 µL NuPAGE® Reducing Agent (10×). The samples were heated at 50° C. for 10 minutes. 5 µL of a premixed molecular weight standard mix, Mark 12 (Life Technologies # LC5677), was loaded in lanes 1 and 2. 15 µL of each prepared fraction from the invention were loaded in lanes 2-13 on the gel. The gel was run according to standard protocols at 125 V for approximately 2 hours. The gel was removed from the cassette and silver stained using standard methods. The results are shown in FIG. 7. Proteins ranging in size from ca. 5-160 kDa are visualized in this example. Furthermore, unique proteins, distinguished by their molecular weight, are found in each fraction.

Figure 8:
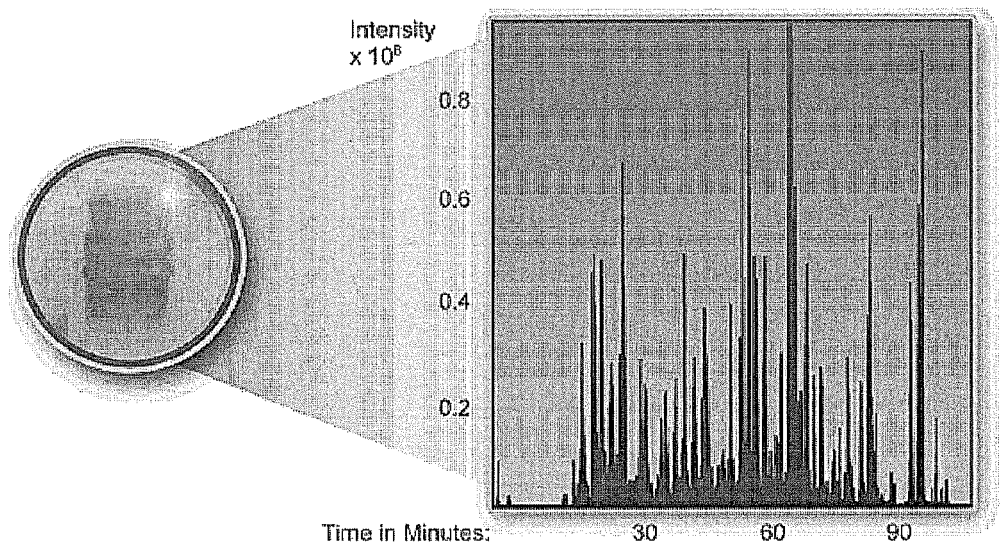
FIG. 8 shows a base peak chromatogram from a single fraction from the gel shown in FIG. 7.
Figure 9:
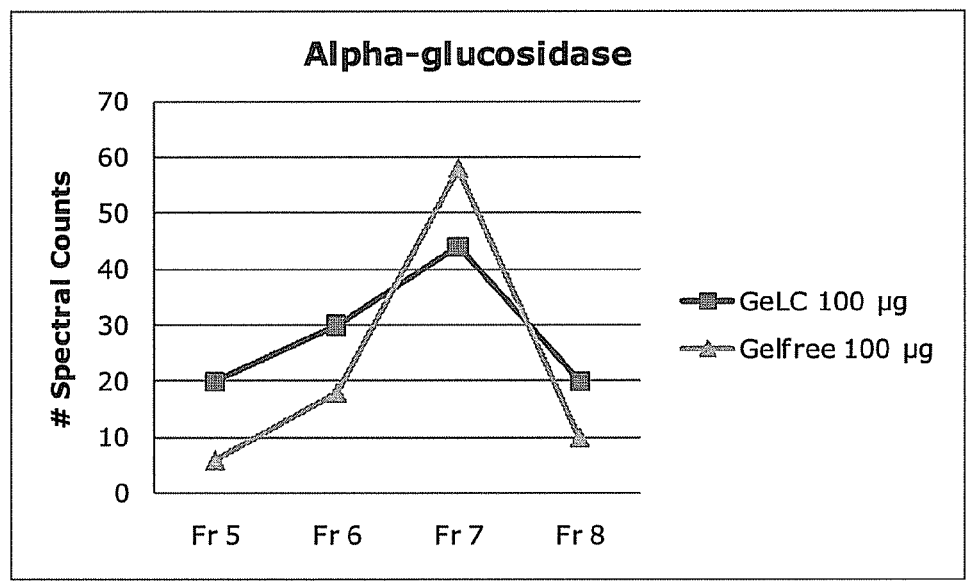
FIG. 9 is a plot of the elution profile of a single target protein isolated using the method of Example 1.

Aside from visualization of fractionation by 1D gel electrophoresis, fractions were analyzed using LC-MS. Prior to LC-MS analytes, SDS was removed from the resulting fractions using the precipitation protocol described by Wessel and Flugge. Following precipitation, the resulting pellets were reconstituted in 50 µL of 100 mM NH4HCO3, reduced, alkylated, and digested overnight at 37° C. Digests were stopped through acidification with formic acid and then concentrated through solvent evaporation to a final volume of 15 µL per sample. A 3 pL portion was then injected onto a 150 mm×180 pm i.d. Biobasic C18 column (Thermo Scientific) and separated using a gradient from 2 to $_{40\%}$ B (ACN/0.1% formic acid) over 85 min, followed by a ramp up to 80% B over 5 min. A nanospray 125 source was used to interface to the LTQ linear ion trap mass spectrometer (Thermo Scientific), which was operated in data dependant mode to acquire MS/MS spectra for peptide sequencing. Data were searched using Sequest, with BioWorks 3.2 software, against the *S. cerevisiae* subset of the Uniprot database. Peptides with charge +1, +2, +3 were accepted with Xcorr scores greater than 1.9, 2.2 and 3.75 respectively. The peptides were further filtered with OCn≥0.1, and Rsp<4. A unique peptide sequence was only assigned once. Peptides matching multiple proteins were arbitrarily assigned to the protein with the lowest MW. For confident identification, proteins were only accepted as a positive hit when two or more unique peptides were matched. The MS analysis resulted in a total of 1110 proteins (4891 peptides) identified from the 12 fractions. FIG. 8 shows the total ion current from a single fraction, displaying significant protein ion current. Furthermore, the elution profile of a single target protein isolated using the method is shown in FIG. 9. Alpha-glucosidase was specifically measured using spectral counting techniques and determined to be primarily purified in a single fraction collection interval using the electrophoretic notch filter, fraction 7.

Example 2

Low Mass Fractionation of Yeast Lysate

As previously described, the mass range of the electrophoretic notch filter system of the present invention may be altered by changing the pore size of the sieving matrix. As such, tunable electrophoretic fractions may be generated using this invention with higher resolution in the low mass range by increasing the % T of the sieving matrix. Here, a yeast lysate was fractionated into 12 distinct molecular weight fractions using a 12% T 5% C polyacrylamide gel across the mass range 3.5-60 kDa and the results visualized using 1D gel electrophoresis followed by silver staining.

Generally, the system and sample was prepared exactly as in Example 1 above. However, to account for differing fraction collection intervals for the higher T cartridge, the electrophoretic notch filter system was programmed with the following sequence:

| Step | 1 | 2 | 3 | 4 | 5 | 6 | 7 | 8 | 9 | 10 | 11 | 12 | 13 |
|---|---|---|---|---|---|---|---|---|---|---|---|---|---|
| Voltage (V) | 50 | 50 | 50 | 50 | 50 | 85 | 85 | 85 | 85 | 85 | 85 | 85 | 85 |
| Fraction Interval (min) | 16 | 44 | 3 | 3.6 | 4 | 2.3 | 2.5 | 2.8 | 3.3 | 4 | 7 | 10 | 18 |
| Total Elapsed Time (min) | 16 | 60 | 63 | 66.6 | 70.6 | 72.9 | 75.4 | 78.2 | 81.5 | 85.5 | 92.5 | 102.5 | 120.5 |
| Action/Fraction # | Add RB* | Change RB/1 | 2 | 3 | 4 | 5 | 6 | 7 | 8 | Change RB/9 | 10 | 11 | 12 |

Figure 10:
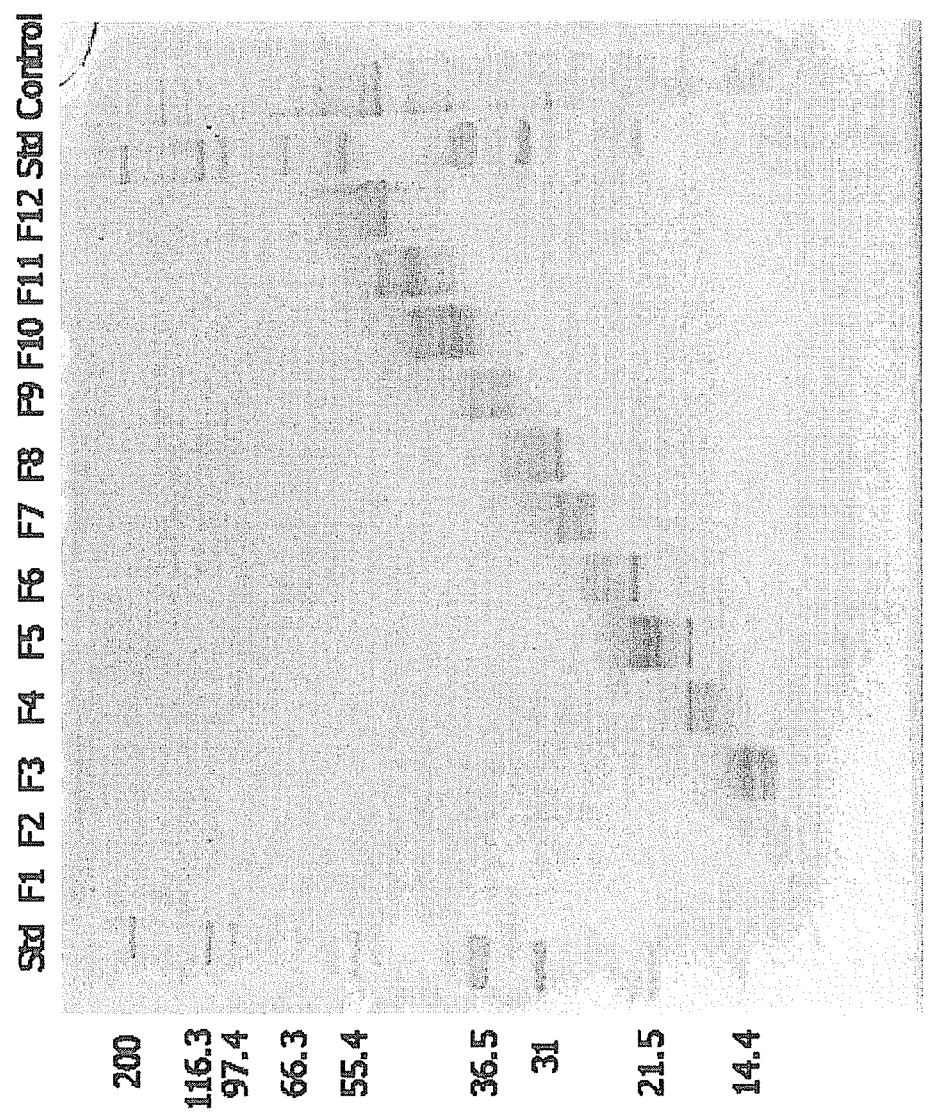
FIG. 10 is a 1D gel visualization of the fractionation of yeast lysate using a 'low' mass protein separation embodiment of the present invention across the mass range 3.5-60 kDa.

Following completion of the fractionation protocol, the sample was prepared as previously described, loaded and separated on a 1D gel, and visualized with silver staining. The results are shown in FIG. 10. Proteins are clearly visible from the mass range 5-55 kDa, demonstrating the unique fractionation afforded by the present invention. Additionally, each fraction has little overlap in molecular weight from those fractions on either side of the collection interval specified.

Example 3

Fractionation of Human Plasma

Human plasma represents an excellent source of potential therapeutic protein biomarkers, since it contains not only blood-borne proteins but also proteins shed from tissues throughout the body. However, it has been well-documented that plasma is perhaps the most difficult of all samples to analyze using techniques such as mass spectrometry, on account of its tremendous dynamic range and inherent analyte complexity. Removal of abundant proteins using affinity depletion greatly reduces sample dynamic range, but alone is insufficient for in-depth proteome analysis using LC-MS. As a result, orthogonal methods must be used to pre-fractionate and/or enrich the sample prior to further separation and analysis using LC-MS. The programmable electrophoretic notch filter system of the present invention was used to partition depleted human plasma into 12 pre-selectable molecular weight fractions with liquid phase recovery of said fractions.

To prepare the sample, plasma (Bioreclamation) was thawed and an aliquot subjected to abundant protein removal using the IgY-12 Abundant Protein Removal Column (Genway), per the manufacturer's instructions. The depleted sample was then concentrated and desalted using a 3500 MW cutoff spin filter (Millipore). Protein concentration was measured using the DC Protein Assay (Bio-Rad Laboratories) and the sample was aliquoted and stored at −80° C. until further use.

A 200 µg aliquot of the depleted sample was thawed and diluted with deionized H2O to achieve a volume of 112 µL. To this sample, 8 µL of 1M DTT and 30 µL of sample buffer as previously described was added, such that the final volume was 150 µL. The sample was heated at 50° C. for 10 minutes.

The programmable electrophoretic notch filter cartridge was prepared as described in Example 1. Prior to use, the plate sealer was removed from the cartridge and storage buffer was removed from all compartments of the desired channel. 8.0 mL of HEPES running buffer was added to the anode and cathode buffer reservoirs of the channel. Next, 150 μL of running buffer was added to the sample collection chamber. A 150 μL aliquot of the prepared sample was then loaded into the sample loading chamber. Care was taken to avoid the introduction of bubbles during loading.

Next, a method was created using the programmable electrophoretic notch filter touch screen interface, as outlined below.

| Step | 1 | 2 | 3 | 4 | 5 | 6 | 7 | 8 | 9 | 10 | 11 | 12 | 13 |
|---|---|---|---|---|---|---|---|---|---|---|---|---|---|
| Voltage (V) | 50 | 50 | 50 | 50 | 100 | 100 | 100 | 100 | 100 | 100 | 100 | 100 | 100 |
| Fraction Interval (min) | 16 | 41.5 | 2 | 2 | 3 | 2 | 2 | 3 | 5 | 7 | 10 | 15 | 20 |
| Fraction # | — | 1 | 2 | 3 | 4 | 5 | 6 | 7 | 8 | 9 | 10 | 11 | 12 |

The cartridge was placed in the instrument, the electrodes lowered and the lid closed. The sequence was started by touching 'Start' on the Main Screen. After Step 2, the system automatically paused for collection of the first fraction. Using an 8-channel pipette, 150 μL was transferred from the sample collection chamber to the first column of a 96-well plate. Using fresh pipette tips, the sample collection chamber was washed with 150 μL fresh running buffer. The sample collection chamber was then filled with 150 μL of fresh running buffer and the sequence resumed. The process was repeated for all remaining fractions. Running buffer was changed after steps 3 and 11 to ensure stable buffer pH.

Figure 11:
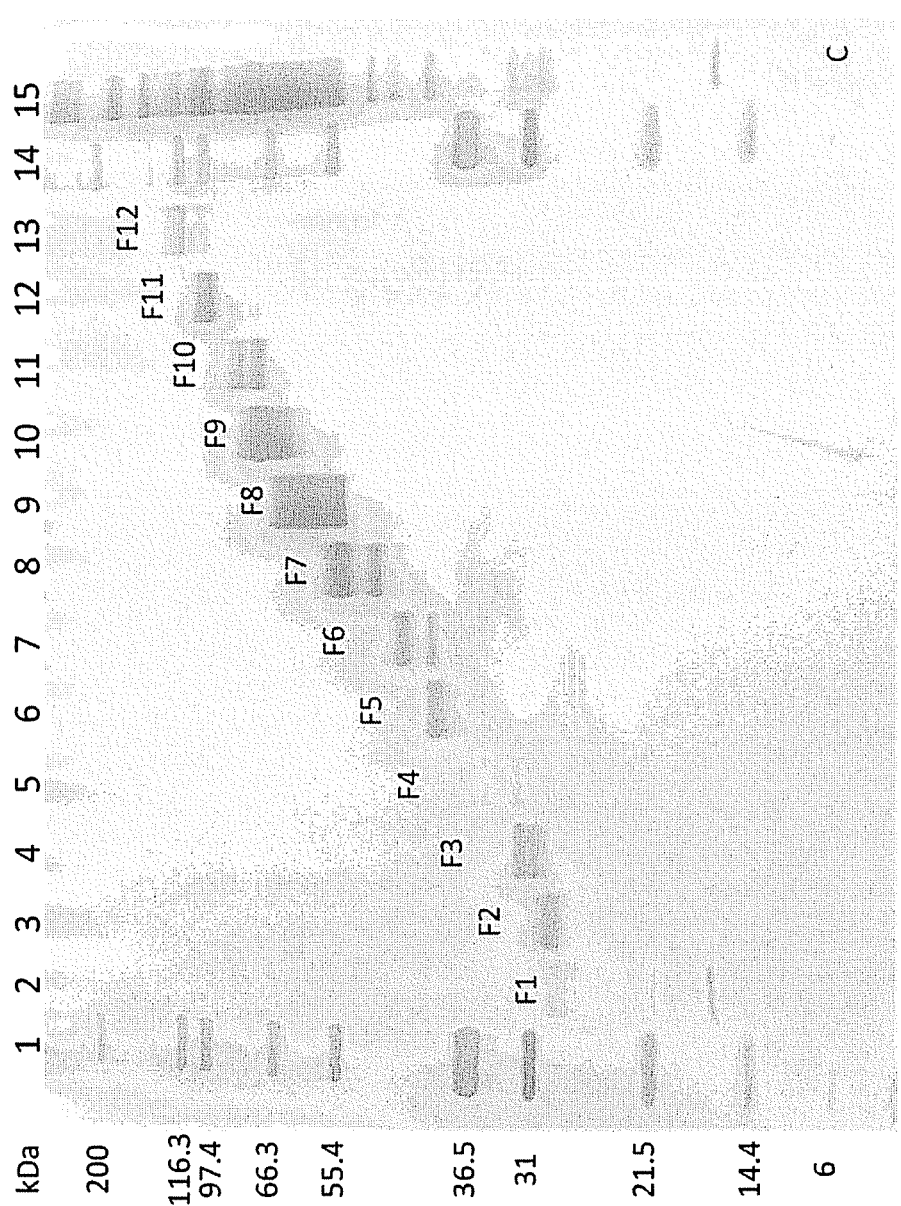
FIG. 11 is a 1D gel visualization of gel depleted human plasma fractionated using an embodiment of the present invention.

The results of the depleted human plasma fractionation process using the programmable electrophoretic notch filter are shown in FIG. 11. Lanes 1 and 14 contain the Mark 12 molecular weight marker mix. Lanes 2-13 show an aliquot of each of the 12 fractions from the present invention, corresponding to 4% of the total volume of each fraction collected. Lane 15 contains the unfractionated sample. As expected, the IgY depletion column removed a large percentage of the high abundance protein found in undepleted plasma (data not shown). Still, a significant percentage of the overall sample is comprised of high abundance proteins, including albumin at ~66 kDa. The vast majority of the protein contained in the sample is found in the 50-100 kDa range. Despite the large proportion of high abundance proteins found in this range, no protein band is observed in more than two fractions, demonstrating effective isolation, purification and fractionation of the sample.

Example 4

Targeted Isolation and Purification of BSA

As previously described, it is an objective of this invention to provide a means for the programmable isolation and purification of target analytes, e.g. antibodies, for subsequent characterization. In such experiments, it is highly desirable to isolate and purify the target analyte in high purity from other contaminating molecules and to recovery as much target analyte as possible. To demonstrate this utility, the unique features of the present invention were used in order to define the fraction elution interval for the isolation and purification of bovine serum albumin (BSA). To perform the electrophoretic isolation, the cartridge was prepared as previously described in Example 1.

To prepare the sample, BSA (Sigma) was diluted at a series of concentrations spanning 1-25 μg in deionized H2O to achieve a volume of 112 μL. To this sample, 8 μL of 1M DTT and 30 μL of sample buffer as previously described was added, such that the final volume was 150 μL. The sample was heated at 50° C. for 10 minutes.

The programmable electrophoretic notch filter cartridge was prepared as described in Example 1 and the samples loaded in all eight channels of a multichannel cartridge. Running buffers were added. Since the molecular weight of BSA was known to be ca. 66 kDa, a first sequence step was programmed at 100 V for 27 minutes. Next, a series of 10 steps operating at 100 V for 90 seconds each were programmed. The run was started.

At the end of step 1, the instrument automatically paused and the entire volume of the sample collection chambers were discarded. The chambers were washed as previously described and 150 μL of running buffer was pipette into the chambers. At the conclusion of each of the subsequent steps, the entire volume of the sample collection chambers were removed and placed into sequential wells of a 96 well plate, the chambers washed, buffer replaced, and the subsequent steps performed.

To visualize the results, an aliquot of each of the fractions representing 6% of the total fraction volume collected was loaded and run on a 1D gel and visualized with silver staining. The results for 1 μg, 5 μg, 10 μg and 25 μg of total BSA are shown in FIG. 12(a). As depicted, 1 μg BSA is observed to elute over two 90 second fraction collection windows. 5 μg BSA is shown to elute over three 90 second fraction collection windows. 10 μg BSA is shown to elute over four 90 second fraction windows and 25 μg BSA is visible over five 90 second fraction windows. Thus, as expected, the fraction collection interval expands with increasing amount of target protein, corresponding to a wider analyte band.

Plotting the elution in graphical format, it is shown that peak width varies between 2.5 and 8 minutes, full width half max (FIG. 12(b)). Using this information, it is clear that 1 μg BSA eluted over a 2.5 minute window between minute 29 and minute 32.5. 25 μg BSA elutes over a 7 minute collection interval from minute 27 to minute 35. As such, the fraction collection window for all concentrations can be easily defined and the system of the present invention operated so as to collect substantially all of the target analyte in a single fraction.

To that end, one channel (Channel 1) of the electrophoretic notch filter was loaded with 1 μg BSA and another channel (Channel 2) loaded with 25 μg BSA. A sequence was defined for Channel 1 that applied 100 V for 29 minutes for step 1 and a second step of 100 V for 2.5 minutes. A sequence defined for Channel 2 that applied 100 V for 27 minutes and a second step of 100 V for 8 minutes. The system was operated as previously described, with the first fractions after the automatic pause at the completion of step 1 being discarded and the process resumed for step 2.

Figure 12:
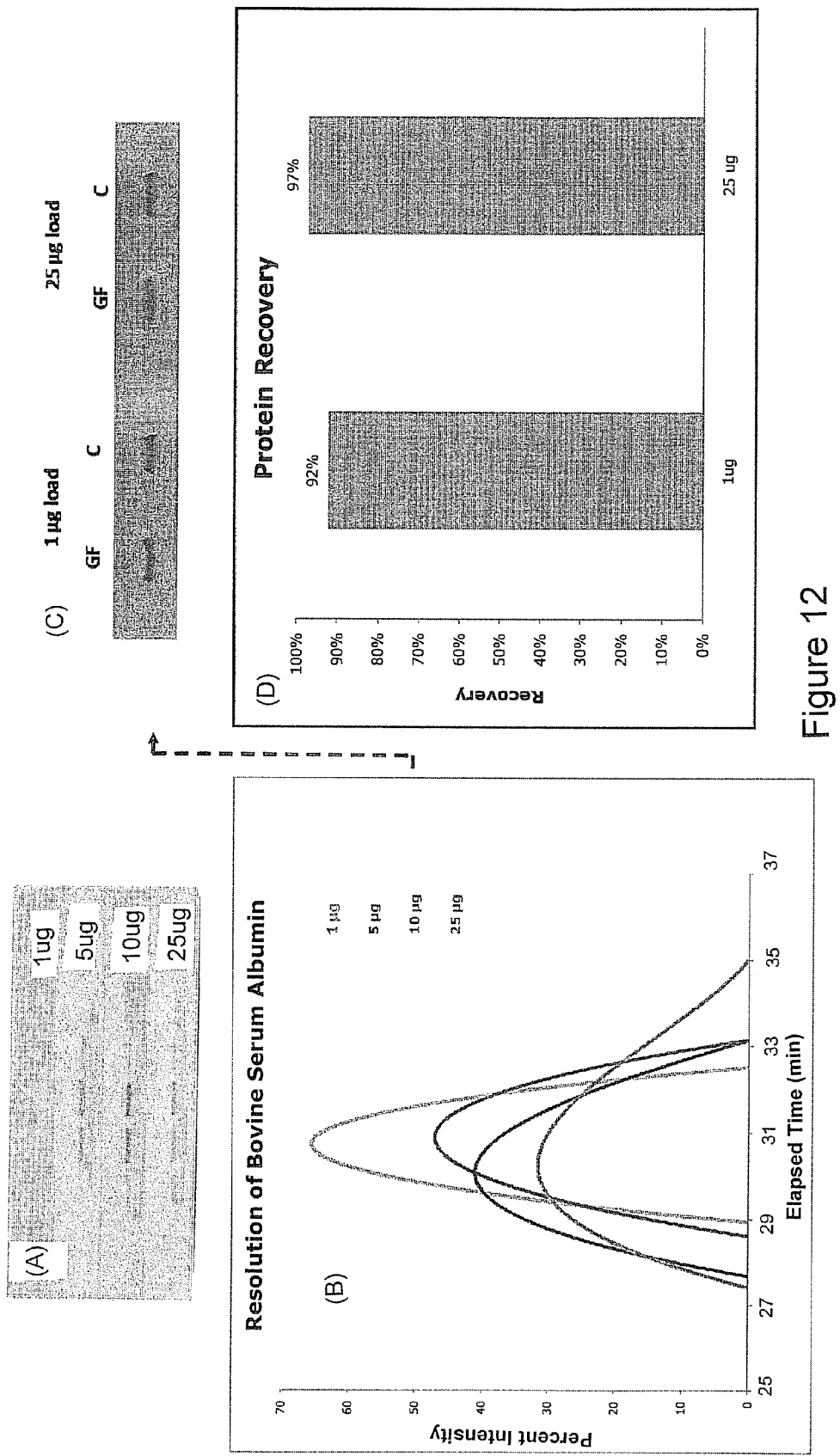
FIG. 12 represents the programmable isolation, purification, and fractionation of a single, target protein using the unique methods of the present invention.

The contents of the fraction collection chambers were collected in both cases after step 2 and visualized on a 1D gel along with a control containing 1 μg and 25 μg BSA, respectively. The results are shown in FIG. 12(c). Clearly, substantially all of the BSA in both cases was isolated and purified from the sample using the programmable electrophoretic notch filter of the current invention. The gel was further scanned and the intensity of each band quantified using commercially available software (BioRad Laboratories). The bar chart in FIG. 12 (d) show the quantity of each collected fraction relative to the control samples, demonstrating >90% recovery in both cases. This example demonstrates the unique features of the present invention to effect a user-programmable isolation and purification of target analytes using electrophoretic mobility-based separation and liquid phase recovery.

Example 5

Separation and Directed Isolation of Analytes Co-Immunoprecipitated

In a related application, it is often desirable to affinity-purify a target sample component for subsequent analytes. Co-immunoprecipitation is one of the most popular methods for affinity purification. However, as is well-known in the art, affinity purification methods often 'pull-down' high abundance, unwanted species along with the target analyte, no matter how specific an affinity ligand is used. As such, one application of the current invention is to further isolate and purify the components from an immunoprecipitation so as to permit more sensitive subsequent preparation or analysis.

In this example, the cartridge was prepared exactly as previously described in Example 1. The sample was NF kappa B p65 immunoprecipitated with conjugated agarose beads, per methods well known in the art. Prepared as 1 µg of immunoprecipitated p65, with associated proteins, bound to antibody-conjugated agarose beads, the sample was dissociated from the beads by incubation in 1×SDS-containing sample buffer. After centrifugation, the supernatant was mixed with DTT to a final volume of 150 µL. This mixed sample was loaded into the cartridge of the present invention and partitioned into 12 fractions using the sequence described in Example 1. The fractions were collected and the process operated as previously described. A 6-µL aliquot of each fraction was analyzed using 1D gel electrophoresis with silver staining.

Figure 13:
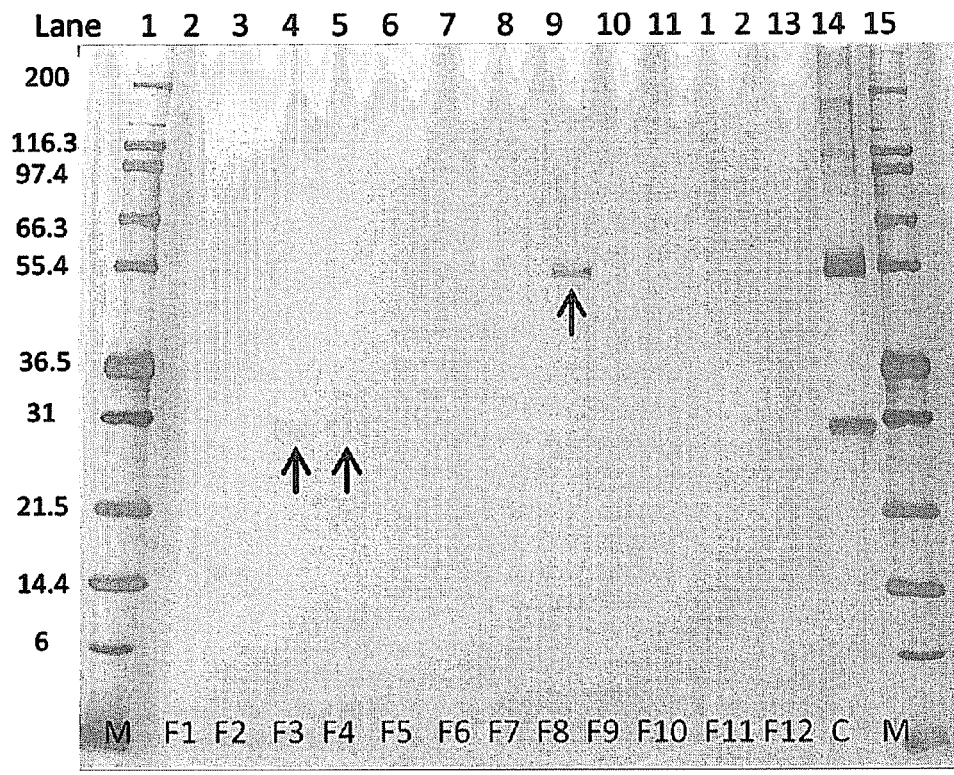
FIG. 13 shows the results of the 1D gel analysis of the fractionated NF kappa B p65 sample as described in Example 5.

FIG. 13 shows the results of the 1D gel analysis of the fractionated NF kappa B p65 sample. Each fraction is represented in a separate gel lane (lanes 2-13). As a control, an aliquot of the unfractionated protein sample, including both supernatant and agarose beads, was loaded in lane 14. Fractions 3, 4, and 8 (in lanes 4, 5, and 9) contain the most abundant proteins of the sample. The protein in fraction 8, near the 55.4 kDa marker, is the target protein at ~60 kDa. The target protein is well resolved from the contaminating protein visible in fractions 3 and 4, near the 31 kDa marker.

Example 6

Evaluation of Reproducibility of Programmable Electrophoretic Notch Filter

System reproducibility is among the most important performance criteria for any preparation system, especially those used to isolate, purify, and fractionate upstream of analytical methods such as ELISA and LC-MS. It is therefore an important aim of the present invention that the methods and devices disclosed herein provide for high reproducibility, channel-to-channel and cartridge-to-cartridge. Overall system reproducibility is dependent on a large number of variables, the most important of which include stability and reproducibility of applied voltage/current, fraction interval time reproducibility as determined by the programmable controller, buffer composition, tube ID/OD, gel composition, and membrane composition.

To characterize the reproducibility of the subject invention, 200 µg of yeast lysate was fractionated according to the procedures and devices of Example 1. Four independent channels were operated—two channels from two different cartridges, in order to assess both channel variability and cartridge variability using a single electrophoretic controller operated sequentially. 12 fractions were collected. Aliquots from fractions 1, 5, and 9 were subsequently subjected to 1D gel electrophoresis and silver staining, as previously described.

Figure 14:
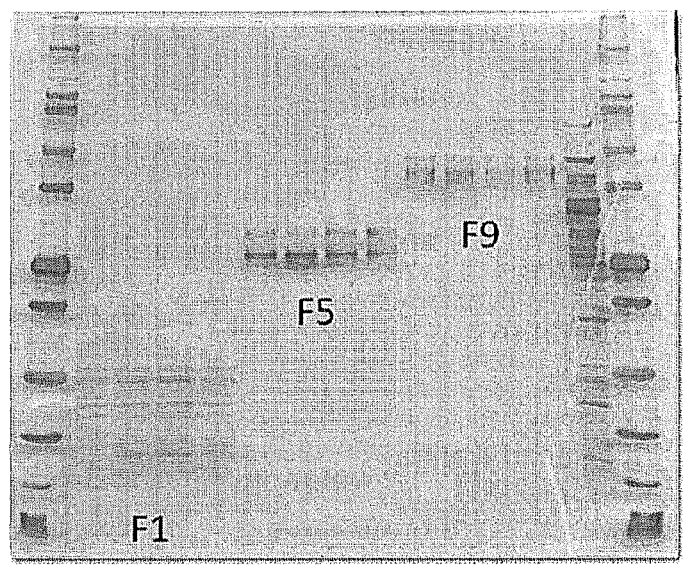
FIG. 14 demonstrates that the reproducibility across each of the channels and cartridges of the present invention.

As shown in FIG. 14, the reproducibility across each of the channels and cartridges is excellent. The upper and lower boundaries of each lane are consistent in each of the quadruplicates in all three fractions, indicating consistent electrophoretic mobility-based elution times. Furthermore, the intensity of each lane is approximately the same. These results demonstrate the unique reproducibility afforded by the present invention for continuous tube gel separation and programmable collection of analytes in liquid phase.

Example 7

Evaluation of Recovery of Programmable Electrophoretic Notch Filter

In addition to reproducibility, recovery is of supreme importance in isolation, purification and fractionation methods for molecular and cellular biology, diagnostics, and therapeutic development, among other applications. In LC-MS, recovery is of particular importance because the amount of protein introduced to the mass spectrometer for analysis will directly correlate to the depth of coverage, sensitivity, for a given sample. Sample preparation techniques that suffer from poor recovery often do so at the expense of the less abundant proteins, which are known to include tissue leakage and interleukins—important proteins in research, diagnostics, and therapeutic development. Likewise, the protein recovered in each fraction must be reproducible. Variation in protein abundance has obvious implications for quantitation and comparative analysis between two samples; reduced variation raises statistical confidence that an observed change is significant.

Recovery was evaluated using two approaches, dictated by the analyte of interest. For peptides below 5 kDa and for selected larger proteins, LC-MS/MS was used to measure recovery. For peptides in the mass range, mass spectrometry has the advantage of being highly sensitive, fast and specific. In the case of larger proteins, digestion is necessary to for LC-MS/MS quantitation to be accurate and sensitive. To measure the recovery of larger proteins, spectroscopy and electrophoresis are the methods of choice. Protein assays that can be measured spectroscopically have the advantage of being fast, easy to carry out, and absolutely quantitative.

In both cases, 5 µg BSA was loaded and run on the electrophoretic notch filter using the devices and procedures outlined in Example 4 in each of 8 channels in a single cartridge of the presented invention. BSA was collected in a single fraction collection window as previously described, and an aliquot of each fraction was analyzed by 1D gel electrophoresis/silver staining. The relative intensity of each band was also measured as previously described using commercially available gel quantitation software.

Figure 15:
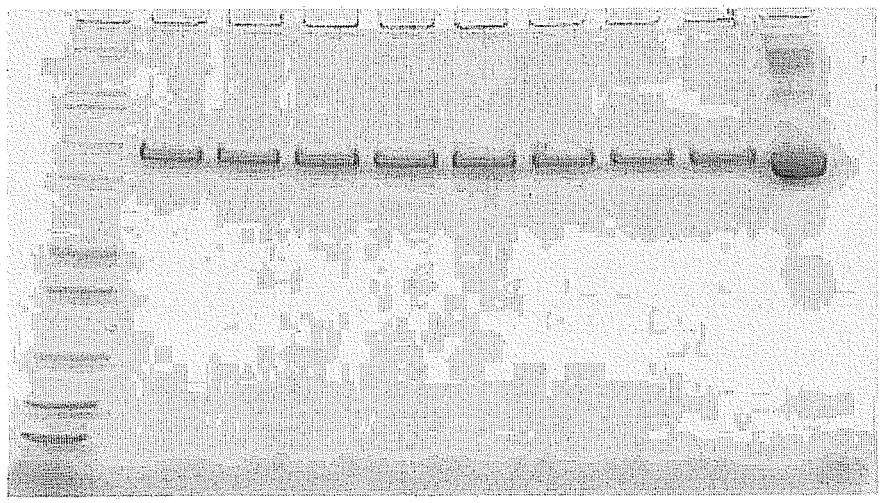
FIG. 15 demonstrates the reproducibility of recovery of BSA across all eight channels of a system and methods of the present invention.

FIG. 15 shows the reproducibility of recovery of BSA across all eight channels. The coefficient of variation of recovery for all 8 samples was determined to be <10%, demonstrating excellent recovery of the target protein. This example demonstrates the unique power of the present invention to isolate and recovery target proteins in programmable, electrophoretic fractions in high yield liquid phase.

Example 8

Fractionation of DNA

While the examples presented heretofore consist of proteins, it will be obvious that the present invention has significant utility in areas outside of protein isolation, purification and fractionation. In one such case, it is desirable to fractionate sheared DNA and isolate, purify and extract in liquid phase DNA of pre-determined base pair lengths. Those fractions are then subjected to amplification so as to create libraries useful in rapid DNA sequencing methods.

To demonstrate the utility of the present invention for DNA fractionation and isolation, a cartridge was prepared as previously describe in Example 1, with the exception that 0.5% agarose was used as the sieving matrix rather than polyacrylamide. Further, only a single layer of sieving matrix was used, rather than a stacking/resolving combination. The gel was prepared using techniques well known in the art, which generally consisted of mixing 0.5% low electro endoosmotic flow agarose (Sigma) with deionized H20 and boiling the solution. The molten agarose was then carefully pipette into the glass tube and allowed to polymerize by cooling to room temperature.

Figure 16:
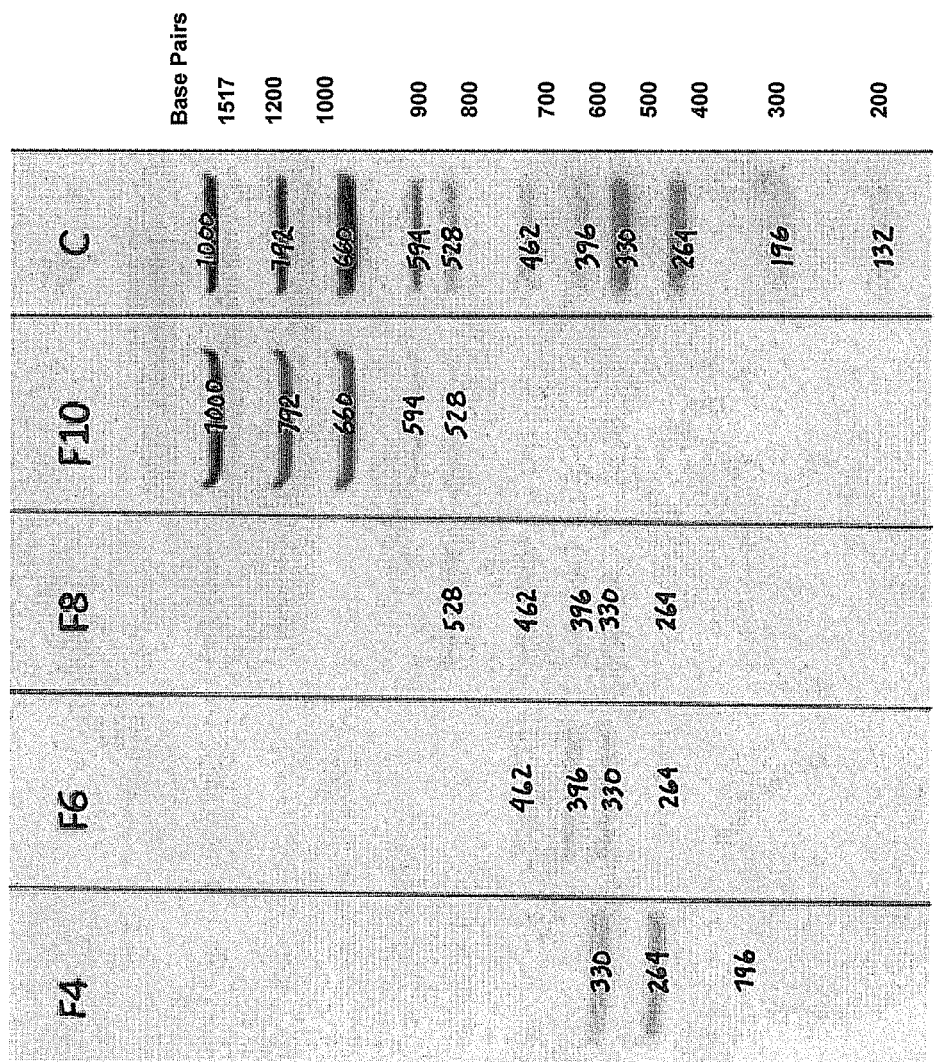
FIG. 16 is a 1D gel visualization of the results for fractions 4, 6, 8, and 10 of example 8 along with a control lane showing the DNA ladder.

The buffer used was a Tris-HCL, pH 7.9 gel buffer with an 50 mM Acetate running buffer. A sequence was programmed into the electrophoretic notch filter controller starting at 85 V for 15 minutes, followed by 85 V for 12 successive 5 minute intervals. Commercially available DNA molecular weight ladder (Sigma) was purchased and mixed with deionized water and a dye, bromophenol blue, to a final volume of 150. The mixed sample was loaded and the fractionation process initiated. Fractions were collected at the end of each predefined step, as previously described. An aliquot of each fraction corresponding to 4% of the total collected volume was loaded onto an Agarose 1D gel (Invitrogen), separated and imaged. The results for fractions 4, 6, 8, and 10 are shown in FIG. 16, along with a control lane showing the DNA ladder. Each fraction contains approximately 3 standards of varying base pairs. The resolution of each fraction can be tightened or widened, depending on the requirements of the specific application. This example clearly demonstrates the utility of the programmable electrophoretic notch filter of the present invention in DNA isolation, purification and fractionation.

What is claimed is:

1. An electrophoretic notch filter apparatus comprising:
  a. a gel cartridge including at least one sample channel, each sample channel including a cathode buffer chamber with an aperture, a sample introduction chamber wherein each sample introduction chamber includes an aperture that passes through the sample introduction chamber and is associated at one end with the aperture of the cathode buffer chamber, a tube gel including a first end associated with the sample introduction chamber, a sample collection chamber associated with a second end of the tube gel and an anode buffer chamber wherein the cathode buffer chamber, the sample introduction chamber, the gel tube, the sample collection chamber and the anode buffer chamber are capable of ionic electrical contact, wherein the diameter of the tube get is between 0.1 mm and 10 mm, and wherein the internal diameter of each tube is consistent from channel-to-channel and cartridge-to-cartridge;
  b. a power supply that is engagable with a cathode buffer chamber of each sample channel and anode buffer chamber of each sample channel;
  c. a user interface for programming one or more steps for a sample channel into a processor wherein programming a step includes programming at least one of a current or voltage that is applied across the sample channel during the programmed step and programming the duration of the application of the voltage or current across the sample channel wherein the programmed one or more steps form a programmed sequence, and wherein the applied voltage is from 1-300 V, and wherein the applied voltage is from 1-300 V; and
  d. an electrophoretic controller including the processor for implementing the programmed sequence, and wherein the applied voltage is from 1-300 V.

2. The electrophoretic notch filter apparatus of claim 1 wherein the user interface is used to program sequences for multiple sample channels and wherein the electrophoretic controller implements the programmed sequences simultaneously.

3. The electrophoretic notch filter apparatus of claim 2 wherein all of the programmed sequences are identical.

4. The electrophoretic notch filter apparatus of claim 2 wherein two or more of the programmed sequences are not identical.

5. The electrophoretic notch filter apparatus of claim 2 wherein none of the programmed sequences are identical.

6. The electrophoretic notch filter apparatus of claim 1 wherein the electrophoretic controller keeps the current or voltage constant during each programmed sequence step.

7. The electrophoretic notch filter apparatus of claim 1 wherein each programmed step includes both a constant voltage or current setting and a voltage or current duration setting.

8. The electrophoretic notch filter apparatus of claim 1 wherein at least one programmed sequence has a plurality of programmed steps and wherein the electrophoretic controller pauses the sequence after a step is complete.

9. The electrophoretic notch filter apparatus of claim 8 wherein the electrophoretic controller pauses the sequence after each step is complete.

10. The electrophoretic notch filter apparatus of claim 1 wherein the electrophoretic controller implements the programmed sequence by controlling power to the electrode.

11. The electrophoretic notch filter apparatus of claim 2 wherein the electrophoretic controller independently controls the power to each of a plurality of electrodes based upon programmed sequence.

12. The electrophoretic notch filter apparatus of claim 8 wherein the electrophoretic controller pauses the sequence by interrupting the power to the electrode.

13. The electrophoretic notch filter apparatus of claim 1 wherein the user interface is a touch screen display.

14. The electrophoretic notch filter apparatus of claim 1 wherein a different cathode buffer reservoir and a different anode buffer chamber is associated with each sample channel.

15. The electrophoretic notch filter apparatus of claim 1 wherein the same anode buffer chamber is associated with two or more sample channels.

16. The electrophoretic notch filter apparatus of claim 1 wherein the cartridge includes a molecular weight cut-off membrane located between the cathode buffer chamber and each sample introduction chamber.

17. The electrophoretic notch filter apparatus of claim 1 wherein including an array of electrodes and an array of counter electrodes wherein the array of electrodes and the array of counter electrodes are each held on moveable arms.

18. The electrophoretic notch filter apparatus of claim 1 including a detector for detecting a feature of a sample located in the sample introduction chamber wherein the electrophoretic controller pauses the implementation of a programmed sequence based upon feedback from the detector.

19. The electrophoretic notch filter apparatus of claim 18 wherein the detector is associated with the gel tube or with the sample collection chamber of a sample channel.

20. The electrophoretic notch filter apparatus of claim 1 including a robotic liquid handling arm for recovering analyte fractions from one or more sample collection chambers.

21. The electrophoretic notch filter apparatus of claim 1 including tubing associated with one or more of the sample collection chambers for recovering analyte fractions from the one or more sample collection chambers.

22. The electrophoretic notch filter apparatus of claim 1 including a cooling means for cooling the gel cartridge.

23. The electrophoretic notch filter apparatus of claim 1 wherein the gel cartridge includes one or more sample collection chambers and one or more sample introduction chambers that are reusable.

24. The electrophoretic notch filter apparatus of claim 1 wherein the gel cartridge includes one or more sample collection chambers and one or more sample introduction chambers that are disposable.

25. The electrophoretic notch filter apparatus of claim 1 wherein the gel cartridge includes a removable seal.

26. The electrophoretic notch filter apparatus of claim 1 wherein the gel cartridge is resealable.

27. The electrophoretic notch filter apparatus of claim 1 wherein the tube gel includes a tubular member filled with a gel.

28. The electrophoretic notch filter apparatus of claim 27 wherein the gel is selected from the group consisting of agarose, polyacrylamide, and a composite mixture thereof.

29. The electrophoretic notch filter apparatus of claim 27 wherein the gel is selected from the group consisting of a single porosity gel, a multiple porosity gel, a single pH gel, a multiple pH gel and combinations thereof.

30. The electrophoretic notch filter apparatus of claim 27 wherein the gel further includes an ingredient selected from the group consisting of dyes, fluorophores, detergents, affinity ligands and combinations thereof.

31. The electrophoretic notch filter apparatus of claim 27 wherein the gel is chemical linked to inside walls of the tubular member.

32. The electrophoretic notch filter apparatus of claim 1 wherein the anode buffer chamber and cathode buffer chamber are each filled with a buffer selected from one or more of Tris, Hcl, Tricine, Acetate, HEPES, TBE, TAE and MOPS.

33. The electrophoretic notch filter apparatus of claim 27 wherein the tubular member is constructed of a material selected from the group consisting of glass, plastic, graphite, ceramic and composites thereof.

34. The electrophoretic notch filter apparatus of claim 1 wherein a fixed volume sample can be horizontally loaded into the sample introduction chamber without dilution, diffusion or trapping of bubbles.

35. The electrophoretic notch filter apparatus of claim 1 wherein the gel cartridge includes notchable pins to permit alignment of adjacent chambers.

36. The electrophoretic notch filter apparatus of claim 1 comprising multiple power supplies for multiple channels, or a single power supply.

37. An electrophoretic notch filter apparatus comprising:
   a. a gel cartridge including at least one sample channel, each sample channel including a cathode buffer chamber with an aperture, a sample introduction chamber wherein each sample introduction chamber includes an aperture that passes through the sample introduction chamber and is associated at one end with the aperture of the cathode buffer chamber, a tube gel including a first end associated with the sample introduction chamber, a sample collection chamber associated with a second end of the tube gel and an anode buffer chamber wherein the cathode buffer chamber, the sample introduction chamber, the gel tube, the sample collection chamber and the anode buffer chamber are capable of ionic electrical, wherein the diameter of the tube gel is between 0.1 mm and 10 mm, and wherein the internal diameter of each tube is consistent from channel-to-channel and cartridge-to-cartridge;
   b. a power supply that is engagable with a cathode buffer chamber of each sample channel and anode buffer chamber of each sample channel, and wherein the power supply applies a voltage of from 1-300 V across each sample channel, and wherein the applied voltage is from 1-300 V;
   c. a detector for detecting a feature of a sample placed in the gel cartridge sample introduction chamber; and
   d. an electrophoretic controller for implementing a sequence for at least one sample channel and for receiving feedback from the detector when the detector detects the sample feature, wherein the electrophoretic controller pauses the implementation of the sequence based upon the feedback from the detector.

38. The electrophoretic notch filter apparatus of claim 37 wherein the detector is associated with the gel tube or with the sample collection chamber of a sample channel.

39. A method for recovering analytes of interest from a biological sample comprising the steps of: forming a gel cartridge including at least one sample channel, each sample channel including a cathode buffer chamber with an aperture, a sample introduction chamber wherein each sample introduction chamber includes an aperture that passes through the sample introduction chamber and is associated at one end with the aperture of the cathode buffer chamber, a tube gel including a first end associated with the sample introduction chamber, a sample collection chamber associated with a second end of the tube gel and an anode buffer chamber wherein the cathode buffer chamber, the sample introduction chamber, the gel tube, the sample collection chamber and the anode buffer chamber are capable of ionic electrical, wherein the diameter of the tube gel is between 0.1 mm and 10 mm, and wherein the internal diameter of each tube is consistent from channel-to-channel and cartridge-to-cartridge;
   locating an electrode in buffer solution in the cathode buffer chamber of at least one sample channel;
   locating a counter electrode in buffer solution in the anode buffer chamber of the same at least one sample channel;
   programming into a processer one or more steps for the at least one sample channel wherein the programming includes programming at least one of a current or voltage that is applied across the sample channel during the programmed step and programming the duration of the application of the voltage or current across the sample channel wherein the programmed one or more steps form a programmed sequence and engaging an electrophoretic controller that includes the processor to implement the programmed sequence, and wherein the voltage applied is from 1-300 V.

40. The method of claim 39 wherein the processor is programmed with sequences for each of a plurality of sample channels and wherein the electrophoretic controller implements the programmed sequences simultaneously.

41. The method of claim 40 wherein the programmed sequences are selected from the group consisting of identical sequences, non-identical sequences and a combination thereof.

42. The method of claim 39 wherein the programming of a step requires the programming of both a constant voltage or current setting and a voltage or current duration setting.

43. The method of claim 39 wherein the apparatus is used for isolating and purifying sheared DNA.

44. The method of claim 39 wherein the apparatus is used for isolating and purifying proteins, peptides, and polypeptides.

45. The method of claim 39 wherein the apparatus is used for isolating and purifying RNA, siRNA, and mRNA.

46. The method of claim 39 wherein the apparatus is used for isolating and purifying DNA and sheared DNA.

47. The method of claim 39 wherein the apparatus is used for isolating and purifying protein complexes.

48. The method of claim 39 wherein the apparatus is used for isolating and purifying components from an immune- or co-immunoprecipitation.

49. The method of claim 39 wherein the apparatus is used for fractionating serum, plasma, proximal fluid, urine, saliva, cerebral spinal fluid, tissue, tissue homogenates, cell lysates, bacteria, plant homogenates and manufacturing process reaction components and results.

50. The method of claim 39, wherein the apparatus has a coefficient of variation of recovery of less than 10%.

* * * * *